(12) United States Patent
Yang et al.

(10) Patent No.: US 7,119,553 B2
(45) Date of Patent: Oct. 10, 2006

(54) SECURITY SCANNERS WITH CAPACITANCE AND MAGNETIC SENSOR ARRAYS

(75) Inventors: Wuqiang Yang, Sale (GB); A. Kathleen Hennessey, Addison, TX (US)

(73) Assignee: Konsulteurope Limited Limited Joint Stock Company, (GB)

( * ) Notice: Subject to any disclaimer, the term of this patent is extended or adjusted under 35 U.S.C. 154(b) by 0 days.

(21) Appl. No.: 11/032,424

(22) Filed: Jan. 10, 2005

(65) Prior Publication Data

US 2006/0176062 A1  Aug. 10, 2006

Related U.S. Application Data

(63) Continuation of application No. PCT/IB04/04414, filed on Jun. 10, 2004.

(60) Provisional application No. 60/477,993, filed on Jun. 11, 2003.

(30) Foreign Application Priority Data

Jun. 10, 2004 (WO) .................... PCT/US04/18385

(51) Int. Cl.
 *G01R 27/26* (2006.01)
(52) U.S. Cl. .................. 324/663; 324/452; 324/71.1; 702/22
(58) Field of Classification Search ............... 324/663
 See application file for complete search history.

(56) References Cited

U.S. PATENT DOCUMENTS 5,552,705 A * 9/1996 Keller .................. 324/239
6,025,726 A    2/2000 Gershenfeld et al.
6,577,700 B1   6/2003 Fan et al.
2002/0038096 A1 3/2002 Gregory et al.
2002/0059022 A1 6/2003 Breed et al.
2003/0156495 A1* 8/2003 Haase et al. .............. 367/119

FOREIGN PATENT DOCUMENTS

WO    WO 02/067015    8/2002

OTHER PUBLICATIONS

Annex to Form PCT/ISA/206 Communication Relating to the Results of the Partial International Search; International Search Authority; Jun. 2, 2005; 5 pages.
U.S. Appl. No. 2002/038096, filed Mar. 28, 2002, Gregory et al.
U.S. Appl. No. 2002/059022, filed May 16, 2002, Breed et al.

\* cited by examiner

*Primary Examiner*—Vincent Q. Nguyen
(74) *Attorney, Agent, or Firm*—Crutsinger & Booth, LLC

(57) ABSTRACT

Security scanning devices based on electrical tomography, including tomography systems based on the measurement of capacitance (ECT) and electromagnetic tomography (EMT), in combination with knowledge-based image analysis and understanding. Each device includes a sensing head or transducer, sensing electronics, image reconstruction and image analysis microprocessor, a display unit and accompanying software for identifying dangerous materials and items. The security scanning devices are employed for obtaining multiple independent measurements and enable implementation of data fusion to combine the complementary sensitivity of ECT and EMT to different material properties, while providing architecture to implement image knowledge bases, which characterize objects, whose image attributes are acquired from multiple sensors.

21 Claims, 14 Drawing Sheets

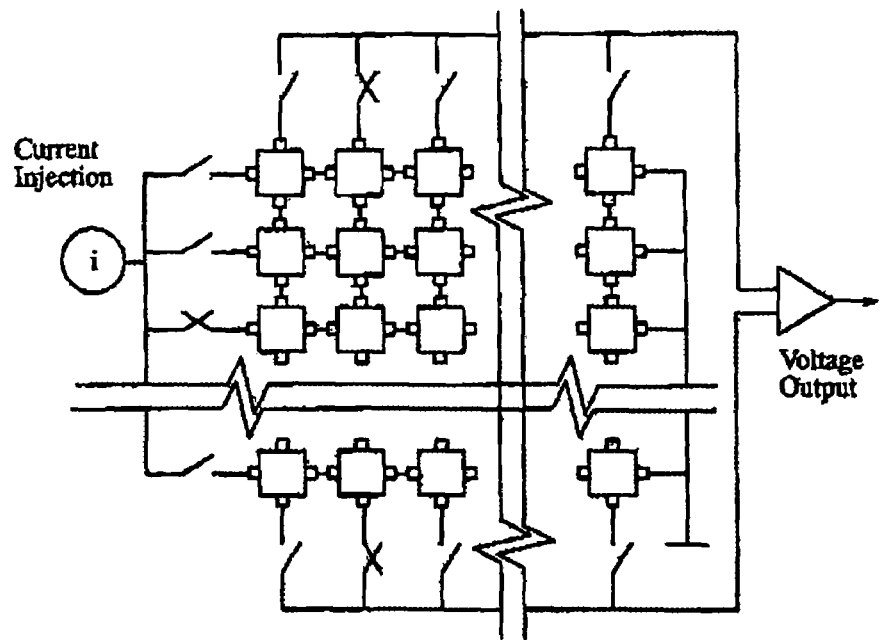
FIG. 4
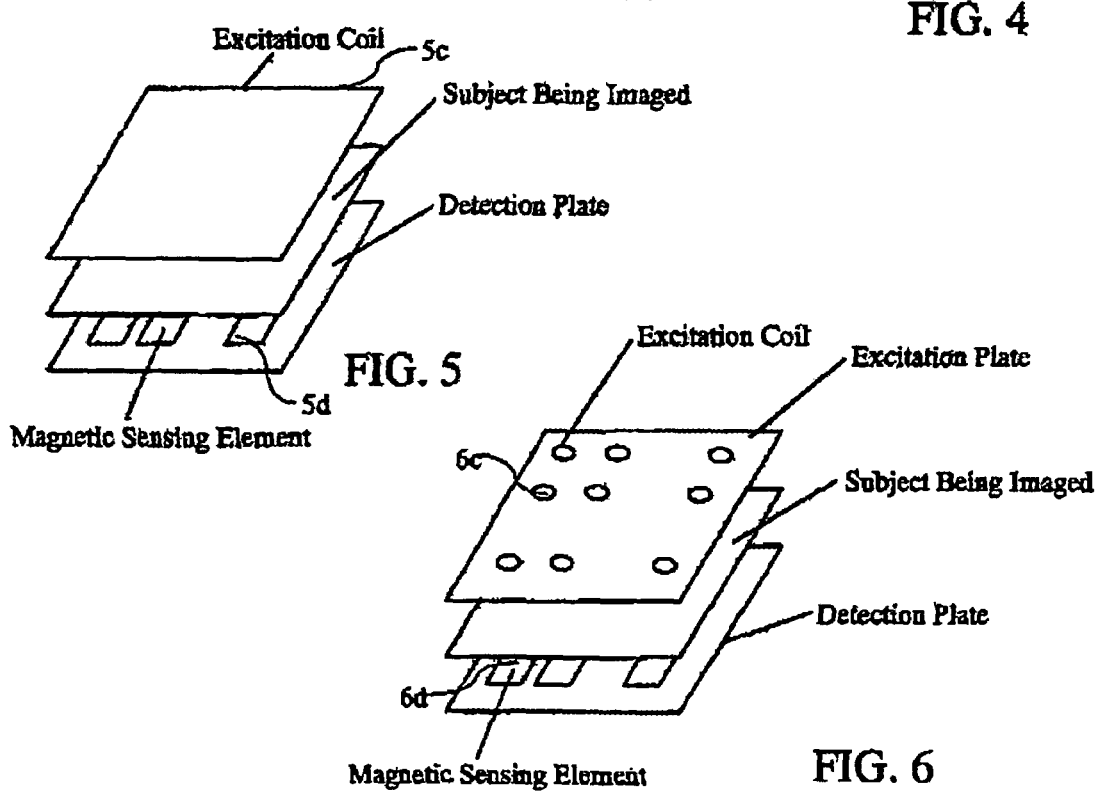
FIG. 5
FIG. 6

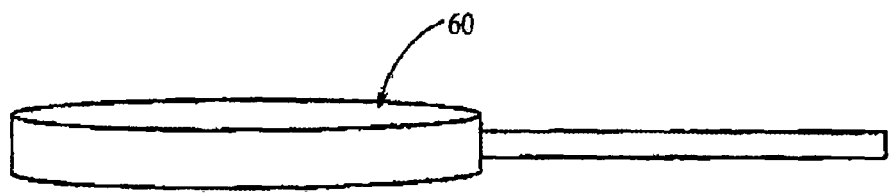
FIG. 21
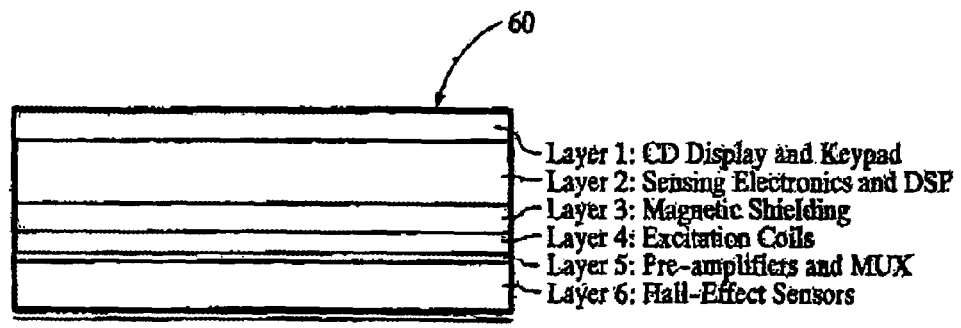
Layer 1: CD Display and Keypad
Layer 2: Sensing Electronics and DSP
Layer 3: Magnetic Shielding
Layer 4: Excitation Coils
Layer 5: Pre-amplifiers and MUX
Layer 6: Hall-Effect Sensors
FIG. 22
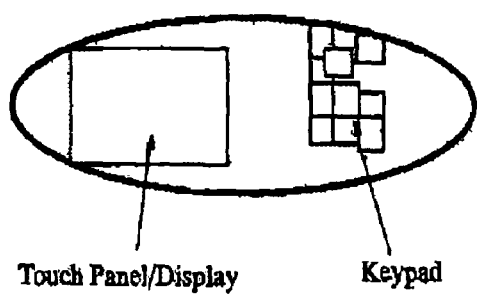
Touch Panel/Display    Keypad    FIG. 23

SECURITY SCANNERS WITH CAPACITANCE AND MAGNETIC SENSOR ARRAYS

This application is a continuation of PCT/IB2004/004414 filed Jun. 10, 2004, which claims the benefit of U.S. Provisional Patent Application No. 60/477,993, filed Jun. 11, 2003.

TECHNICAL FIELD

The present invention relates in general to improvements in apparatus and methods for providing real-time 3D images of the contents of containers, such as envelopes, packages and luggage.

BACKGROUND OF THE INVENTION

The battle against crime and terrorism has necessarily been a high priority for all civilizations. Since Sep. 11, 2001, homeland security has been receiving the highest attention in airports, post offices and other sectors dealing with public access. In the USA, the Department of Homeland Security (DHS) has recently been formed in addition to the FBI and CIA, indicating the priority of the U.S. government to prevent further attacks. In the UK, there have been frequent threats of terrorist attacks on airports.

While x-ray machines are commonly used to check airline passengers' luggage and they are effective in identifying objects of different densities, they have significant problems: (a) there are concerns over radiation exposure. In particular, the members of security staff working on x-ray scanners possibly receive unacceptable radiation; (b) the machines are expensive to purchase and operate. It is estimated that the operational cost is around $1 million a year per x-ray machine, prohibiting their use in less cash-intensive situations; (c) most x-ray machines can only provide 2D images, making it difficult for members of security staff to identify dangerous objects. The images generated must be viewed or assessed by experienced/trained personnel, because no efficient automatic methods are currently available for reliably triggering alarms, and (d) they are bulky and non-portable and security personnel cannot easily check an abandoned bag using an x-ray machine. Therefore, alternative and/or complementary security scanning tools are being sought.

For general aviation, e.g., small airports and non-standard operations, and for sports events or public theaters, it is not realistic to use x-ray machines routinely. The most popular tool used for security checking is the metal detector. Although metal detectors are very sensitive to ferrite materials, they cannot give information on shape and/or size and cannot detect non-metal objects (e.g., a ceramic knife) and chemical substances (e.g., explosives). These limitations of the currently-available detectors prevent the identification of dangerous objects and materials. In many other cases, it is also necessary to check bags and people for security reasons, e.g., to control access to train stations, government buildings, and even buses.

Neither post offices nor parcel delivery services currently have any tool for checking the contents of envelopes, packages and boxes. Bombs, anthrax, guns and other illegal materials have been sent through post offices and delivery services. This indicates the necessity of developing technology and security scanning tools to address this problem. To detect explosives and chemical substances, various chemical sensors have been developed, such as the Ionscan machine from Smith Detection (Elliot and Goetz 2003). These tools are designed to check for vapours from biological and dangerous chemical materials. However, if the explosive or chemical substances are well sealed, the chemical sensors will not detect them.

In the USA, InVision Technologies, Inc. has developed CT scanner machines for security applications, based on x-ray sensors (InVision 2003). The sensing principle of such machines is the same as the commonly-used x-ray machines, but can provide tomographic 2D and 3D images. However, those machines possess all the disadvantages of the commonly-used x-ray machines: radiation, expense and bulk. X-ray tomography sensors have to take measurements over extended periods of time, so that a usable set of data can be recorded to produce an acceptable image. Recently, InVision announced a new machine, QScan QR 500, which is based on quadrupole resonance analysis. In principle, this is similar to magnetic resonance imaging (MRI). Instead of using a magnet, quadrupole resonance analysis makes use of low intensity pulses of carefully tuned radio waves to probe for the molecular structure of target materials (InVision 2003). However, this type of machine is limited to the detection of some liquid explosive materials only, and is huge in size and massive in weight, a few tons.

The use of penetrating non-ionizing radiation for security checking, such as millimeter-waves, has also been proposed (QinetiQ 2001). Although the organizations involved assert that this is non-harmful radiation, it is well established that any millimeter-wave or microwave radiation is potentially harmful because the operating frequency is as high as 35 or 94 GHz (QinetiQ 2001). At the Pacific Northwest National Lab in the USA, similar scanners using millimeter-wave radiation have also been announced. They declared that the scanner allows security personnel at airports to "see" the full spectrum of concealed weapons, including non-metallic threats, such as plastics, explosives and ceramic knifes. Legitimate safety concerns, which have not been adequately addressed, would allow individuals to refuse to be "microwaved". This would prevent security agencies from insisting on scanning everyone.

Tomography has been widely used in hospitals for diagnosis purposes. An x-ray CT scanner can provide 2D and 3D images of objects inside a human body. In recent years, industrial process tomography (IPT) has developed rapidly. While the principles of IPT are similar to medical tomography, there are some key differences: (a) IPT systems may be optimized to sense properties other than just density, e.g., contrast in dielectric properties, thus distinguishing different plastics; (b) IPT systems may acquire only a few dozen measurements per image. Whilst this yields images of relatively poor spatial resolution, the temporal resolution is very good, in the order of milliseconds; and (c) IPT systems are small, portable and relatively low cost.

Among IPT techniques, electrical tomography, which measures permittivity, conductivity and permeability and accordingly are called electrical capacitance tomography (ECT), electrical resistance tomography (ERT) and electromagnetic tomography (EMT), offers several advantages: rapid response, low-cost, non-intrusive and/or non-invasive, and robustness in hostile environments. Electrical tomography has been used for many research applications, such as imaging of gas-oil two-phase flows in pipelines, gas-solids distribution in pneumatic conveyors and fluidised beds, combustion flames, liquid—liquid and solids-liquid mixing processes and personnel landmines (York 2001). The main weakness of electrical tomography is that it uses a relatively small number of sensing elements (typically 8, 12 or 16), because of the limitation in the sensitivity of electronic circuits. As a result, the number of independent measurements is usually limited to say <100, and, hence, the present electrical tomography systems can only provide moderate spatial image resolution.

Although tomography has been utilized in industrial and medical applications for producing images of the interiors of opaque objects over the past 35 years, characteristics of current tomography technology have limited its utility. The problems inherent in the sensors themselves include: (1) excessive size and weight of sensor devices using radiation, (2) safety of living tissue in scanned objects, and (3) low resolution of sensor signals. Other problems associated with the process, by which the sensor signals are converted into useful information, include: (1) integration of control of motion of object with sensor signal capture cycles, (2) cost of the entire apparatus, (3) lengthy time required between generation of sensor signal and creation of useful image, and (4) inability to distinguish among different types of materials.

There exists a need for new and improved security scanning devices for non-invasive checking of the contents of containers, and particularly luggage at transportation, freight and mail facilities.

SUMMARY OF THE INVENTION

The method and apparatus of detecting concealed dangerous objects in luggage or other enclosures generally comprises scanning known objects with capacitive and inductive sensors. The sensors are preferably mounted in or on a transducer that may be portable or stationary. Changes in capacitance or inductance in the vicinity of the sensors are recorded in a computer database when each of a plurality of known objects is positioned in the vicinity of the sensors. Image and knowledge databases are built containing data regarding each of the known objects. The database is indexed and data is used for back propagation, a form of supervised learning, for imaging and identifying concealed objects. Error data at the output from the sensors is used as feedback to earlier ones, allowing incoming weights to be updated.

When luggage containing unknown objects is scanned, using capacitive and inductive sensors, changes in capacitance and inductance in the vicinity of the unknown objects is compared with data in the image and knowledge databases. Limited data regarding the character, texture and shape of the object causes the computer to change the excitation signals to facilitate creating images of the unknown object and determining whether or not the object is a dangerous object. Providing feedback allows the system to optimize performance in image generation by different measurement protocols and different excitation frequencies delivered to the sensors. By means of the image knowledge-base technology, real-time image analysis may be achieved, including detection and identification of dangerous objects. The operator can rotate the 3D images of concealed objects to permit rapid identification.

British Patent Number GB2329476 to Wu Qiang Yang, entitled "Image Creation in a Tomography System," discloses a method and apparatus for creating an image from data obtained using electrical capacitance tomography. The patent discloses a electrical capacitance tomography (ECT) system for producing an image of a cross-section of a conduit surrounding dielectric materials of different relative permittivities. The patent states that a series of measurements of capacitance across a conduit is obtained by exciting electrodes positioned around an outer wall of the conduit. The capacitance measurements are used to construct an image of a section through the conduit which represents the relative proportions and location of dielectric materials within the conduit.

British Patent Number GB2329476 to Yang obtains an image of a cross-section of a conduit surrounding dielectric materials of different relative permittivities by using electrical capacitance tomography sensor array distributed around a section of the conduit. The sensor array comprises a series of electrodes which provide measurements of capacitance between different pairs of electrodes across the section of the conduit. The capacitance measurements are used to create an image using a technique known as Linear Back Projection (LBP).

This British Patent states that the LBP algorithm for a mixture of a low permittivity material and a high permittivity material is expressed by the equations disclosed where:

N is the number of measurement electrodes comprising the sensor array;

F(p) is the fraction of high permittivity material present at a position p within the cross-section of the conduit;

Sjj(p) is the sensitivity of a pair of electrodes to a change of permittivity at a position p within the cross-section of the conduit;

Cij' is the capacitance between a pair of electrodes when the conduit is filled with low permittivity material;

Cijh is the capacitance between a pair of electrodes when the conduit is filled with high permittivity material;

Cijm is the capacitance between a pair of electrodes during measurement; and

Rjj is the normalized change in capacitance.

The variable Sjj(p) is determined for each position p within the conduit by measuring the effect of permittivity changes for each pair of electrodes. The resulting set of values is commonly referred to as a sensitivity map, a separate map being produced for each pair of electrodes. The LBP algorithm produces an image of a section through the conduit by linearly superimposing the sensitivity maps for each electrode pair using capacitance measurements as weighting factors.

An LBP image reconstruction algorithm is shown schematically in FIG. 1 of the patent, where X represents a set of normalized capacitance changes measured from the electrodes, S is the set of sensitivity maps, and F is an image which represents a normalized permittivity distribution. The LBP reconstruction algorithm can be considered as a multi-variable open loop system.

Although the LBP algorithm is unable to produce an accurate quantitative image, it does provide a useful qualitative image. The present embodiment of the invention uses an image reconstructed by the LBP algorithm to provide an initial set of values for a subsequent iteration process. Since the LBP algorithm is not an accurate mathematical expression relating the measured capacitance values and the image, the image reconstructed by the LBP algorithm must differ, to some extent, from the actual permittivity distribution. Consequently normalized capacitance changes calculated from the reconstructed image assuming that the image accurately represents the distribution will differ from the capacitance changes measured from the sensor. These differences between the measured and calculated capacitance values are used as inputs for the iteration process.

The present invention relates to improvements disclosed in British Patent Number GB2329476 to Wu Qiang Yang, entitled "Image Creation in a Tomography System," the disclosure of which is incorporated herein by reference in its entirety for all purposes.

A primary object of the invention is to provide a method and apparatus for enhancement of image resolution with ECT and EMT, wherein more sensors, more sensitive circuits and flexible/optimal measurement protocols are employed for obtaining more independent measurements.

Another object of the invention is to provide a method and apparatus for implementation of data fusion to combine the complementary sensitivity of ECT and EMT, possibly together with x-ray, to different material properties.

Another object of the invention is to provide a method and apparatus using optimal techniques for noise filtering, feature extraction, construction of objects and 2D and 3D, generation of their attributes, and production of feedback signals to multiple image generation units, which utilize a variety of imaging technologies.

A further object of the invention is to provide a method and apparatus using architecture and implementation of image knowledge bases, which may characterize objects, whose image attributes are acquired from multiple sensors.

A still further object of the invention is to provide a method and apparatus for real-time operation with a large number of sensors, with parallel measurement channels and parallel data processing.

The invention disclosed herein provides a method and apparatus for solving these problems, thereby increasing the potential utility of tomography in a variety of applications, of which four preferred embodiments are described herein: (1) 3D capacitive scanner with parallel sensor arrays, (2) planar sensor capacitance array, (3) magnetic scanner with planar Hall-effect sensor array, and (4) multi-plane ECT for 3D imaging of metal objects and chemical substances.

DESCRIPTION OF THE DRAWINGS

Drawings of four preferred embodiments of the invention are annexed hereto so that the invention may be better and more fully understood, in which:

FIG. 4 is a diagrammatic view of switching for sensors;

FIG. 5 is a diagrammatic view of a Hall transducer with multiple magnetic sensing elements;

FIG. 6 is a diagrammatic view of a Hall sensing device with multiple coils and magnetic sensing elements;

FIG. 21 is an orthogonal view of an hand-held scanner;

FIG. 22 is an expanded side view of a hand-held scanner with multi-layers;

FIG. 23 is a top view of a hand-held scanner;

Numeral references are employed to designate like parts throughout the various figures of the drawing.

DESCRIPTION OF A PREFERRED EMBODIMENT

Figure 1:
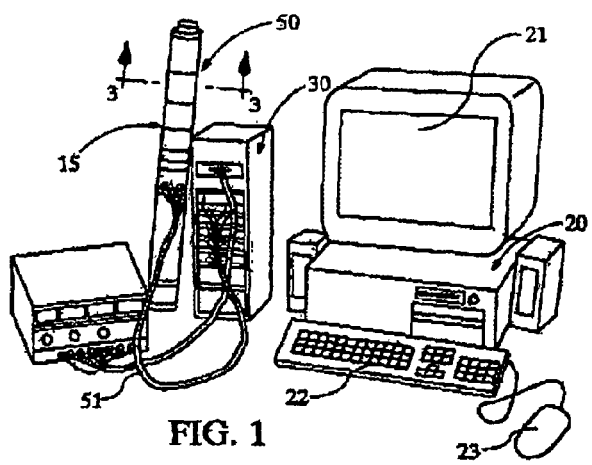
FIG. 1 is a perspective view illustrating the security scanning device.

Referring to FIG. 1 of the drawings, the numeral 15 generally designates a security scanning device comprising a computer 20, a data acquisition module 30, an interface 40 and a transducer 50, having sensors mounted for detecting changes in capacitive or inductive fields in the vicinity of the transducer 50. Transducer 50 is preferably connected to the data acquisition module 30 by a cable 51 or wireless transceiver (not shown).

In a preferred embodiment, security scanning device 15 is based on electrical tomography (more specifically ECT and EMT) and knowledge-based image analysis and understanding, each device comprising a sensing head, sensing electronics, image reconstruction and image analysis microprocessor (either microcontroller, DSP, laptop or desktop PC), a display unit and accompanying software.

Computer 20 is preferably a general purpose machine that processes data according to a set of instructions that are stored internally either temporarily or permanently. Computer 20 is preferably a personal computer, laptop or handheld device. However, computer 20 may assume any configuration and preferably includes a VGA display or monitor 21, input/output devices such as keyboard 22, and mouse 23, data storage devices and CPU processors to calculate, compare and copy data, along with slots for various peripheral devices.

Computer 20 preferably has a communications capability to use a wide area network to update the system and to check for updated definitions, patches and new features, device drivers, and system updates available from a central server.

Figure 2:
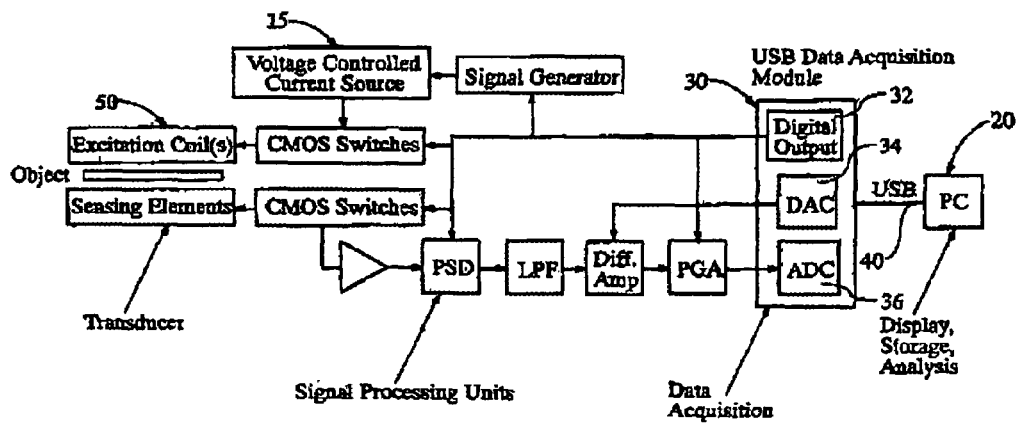
FIG. 2 is a block diagrammatic view of the security scanning device.
Figure 7:
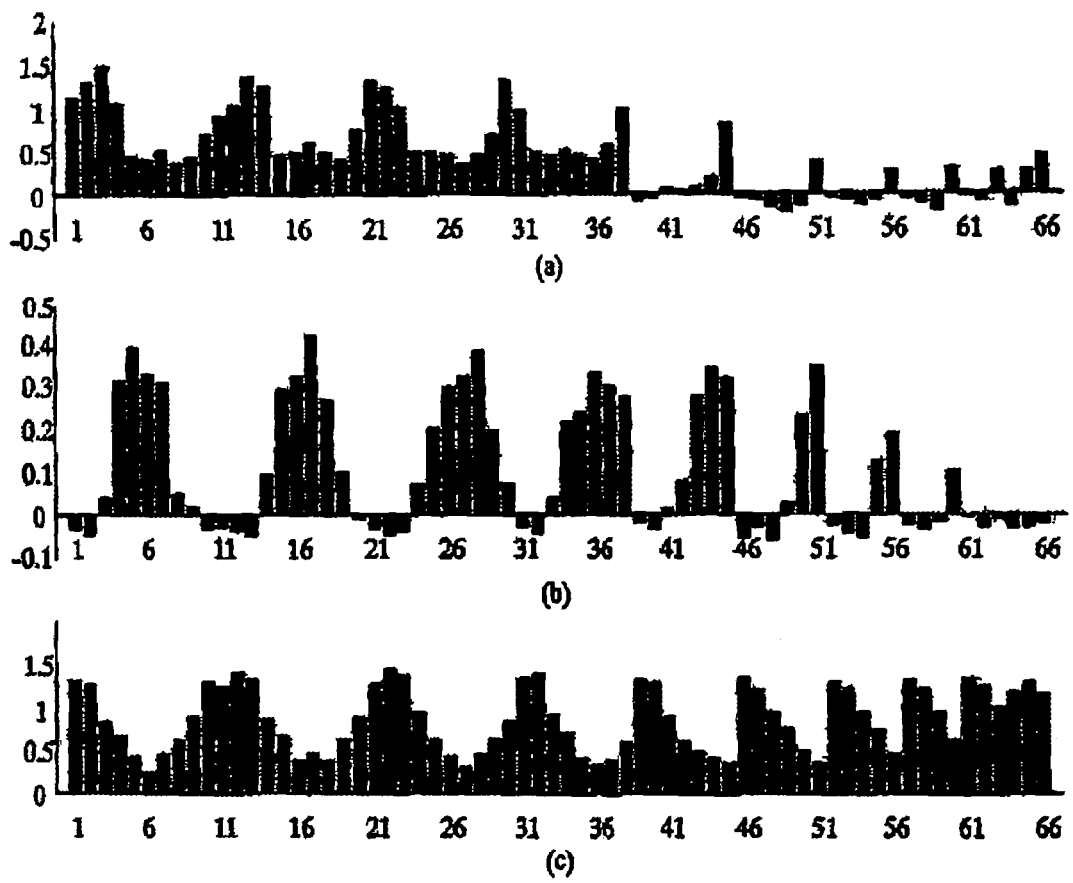
FIG. 7a is a graph showing stratified distribution.
FIG. 7b is a graph showing core distribution.
FIG. 7c is a graph showing annular distribution.
Figure 11:
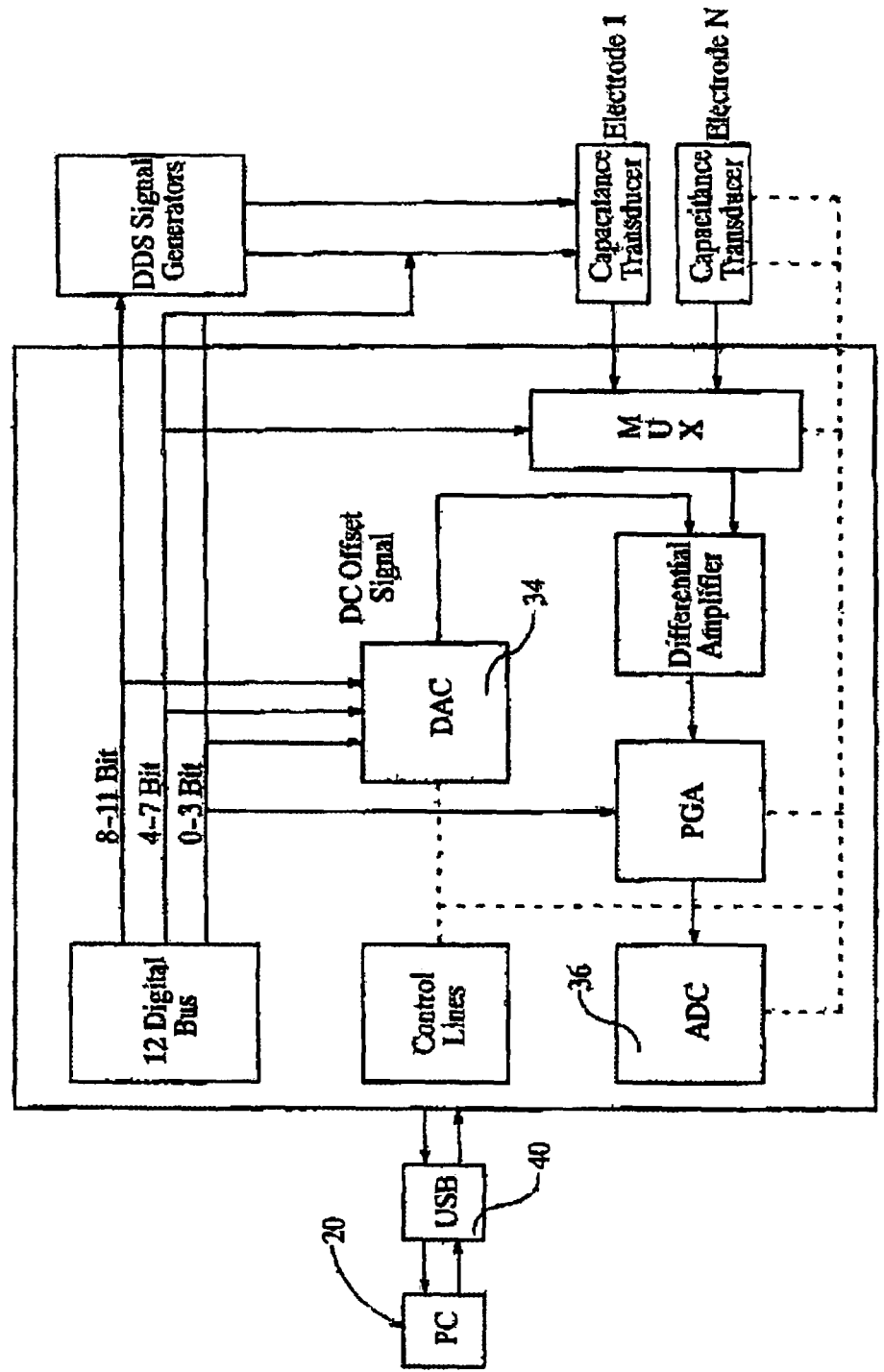
FIG. 11 is a diagram of a data acquisition system showing the USB interface card.

As best illustrated in FIGS. 1, 2 and 11, data acquisition module 30, preferably includes a digital output device 32, digital-to-analog converter (DAC) 34, and an analog-to-digital converter (DAC) 36.

In the illustrated embodiment, the interface 40, between the computer 20 and the data acquisition module 30, is a USB interface, as illustrated in FIGS. 9–18.

Figure 9:
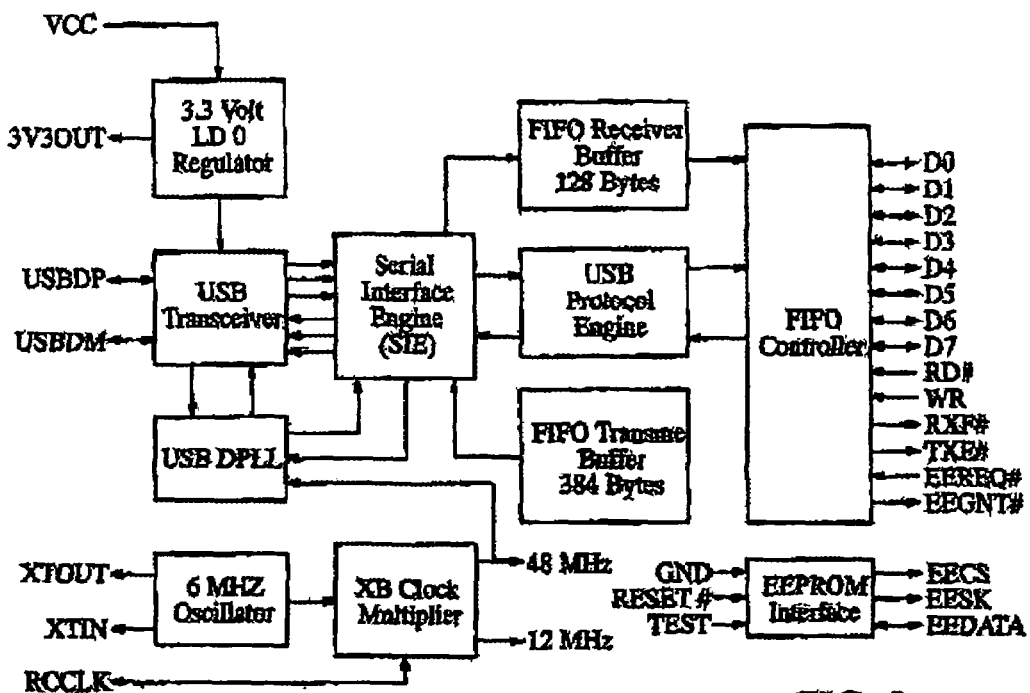
FIG. 9 is a diagram of an internal block of USB-IFM.

The data acquisition card is designed, based on an USB interface module (USB-IFM) MOD2 with an FT8U245AM integrated circuit (IC) chip on it from Future Technology Devices International (FTDI) Ltd. in Scotland [1]. USB-IFM was selected because it provides an easy and cost-effective way of transferring data between peripheral devices and a PC 20 at up to 8 Mbits (1 Mbyte) per second and its simple FIFO structure. The accompanying software makes it easy for the users, who may not be familiar with the protocols of USB, to control other devices via I/O ports. FIG. 9 is a block diagram of the USB-IFM.

Figure 10:
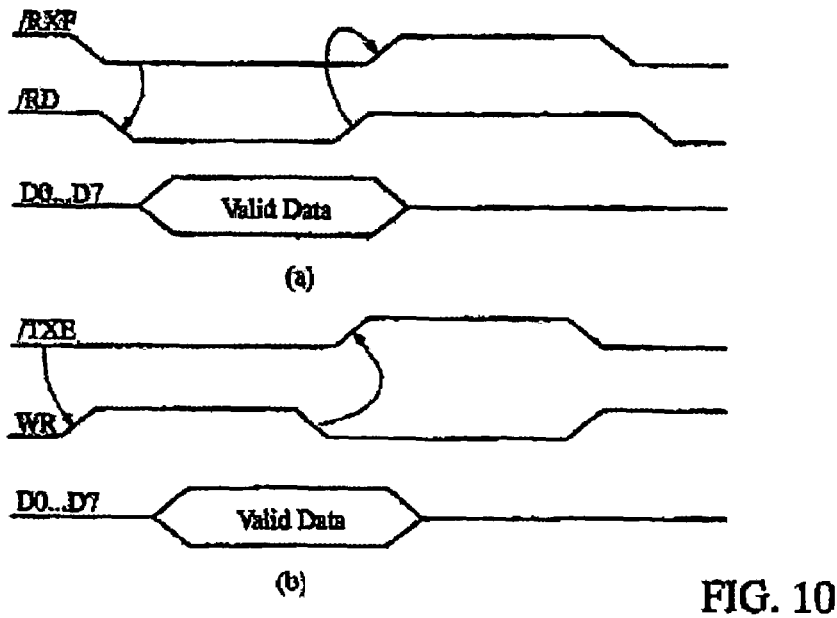
FIG. 10 is a USB-IFM timing diagram.

USB-IFM communicates with a PC 20 via a USB link and with the peripheral devices via an 8-bit parallel data port (D0–D7). All low level operations involved in transmitting data between the USB-IFM and the PC 20, including the transitions between serial and parallel data, are handled internally by the USB-IFM. When the PC 20 sends data to the USB-IFM, the data is stored in the FIFO Receive Buffer and can be read by the peripheral from the data port one byte at a time. Each rising edge of the RD# signal sent to the USB-IFM causes a new byte to be transferred to the data port, as shown in FIG. 10a. The peripheral sends data to the USB-IFM for transmission to the PC 20 by writing one byte at a time onto the data port. Each falling edge of the WR signal sent to the USB-IFM causes the byte to be transferred to the FIFO Transmit Buffer (see FIG. 10 (b)).

The RD# and WR Signals must be generated by the peripheral. Two signals, RXF# and TXE#, are automatically generated by the USB-IFM to control the data flow. When the TXE# flag is "1", data cannot be written onto the USB-IFM data port. Similarly, when the RXF# flag is "1", data cannot be read from the USB-IFM data port.

The overall data acquisition system 30 is shown in FIG. 11, which includes the data acquisition card, a signal generator card, and up to 6 capacitance measurement cards, providing twelve capacitance measuring channels, one for each capacitance electrode. Two direct digital synthesizer (DDS) IC chips (AD7008) are used to generate two synchronized 500 kHz sine-wave signals of 18 V peak to peak, one as the excitation source and the other as the reference signal for phase sensitive demodulation (PSD). The analogue multiplexer (MUX) (ADG526) is used to select the DC signal from each capacitance measurement channel in sequence. A differential amplifier (INA105) subtracts the appropriate voltage produced by a 12-bit digital-to-analogue converter 34 (DAC) to cancel the standing capacitance. The signal now represents the measured change in capacitance and is further amplified. A DC PGA with selectable gains of 1, 2, 4, 8, and 16 is required to deal with a large dynamic measurement range. The analogue signal is finally converted to a 12-bit digital signal by an analogue-to-digital converter (ADC) and then transmitted to the PC 20 in two bytes.

The offset signal, which is used to balance the standing capacitance, comes from the DAC 34, which is on the data acquisition card. The offset signal can vary from 0 to 5 V in 4096 steps, and is expressed as:

$$T^1 = T^1_{ref} \frac{D}{2^{12}} \quad (1)$$

where $V_{ref}$ is the reference voltage for the DAC 34 and D is the digital input.

The ADC is configured for offset bipolar operation and operates over the range $V_m = -1$ V to 4 V. The digital reading is given by:

$$E = \frac{-T^1_m + 4}{F} 2^{12} \quad (2)$$

where F is the full measurement range of the ADC.

System operation is controlled by the digital outputs port on the data acquisition card and provides the following functions:

(1) Control of CMOS switches to select the excitation and detection electrodes;

(2) Control of the amplitude and frequency of the excitation and the reference signals and the phase difference between them;

(3) Control of the MUX to select the DC signals in turn, from the capacitance measuring circuits; and (4) Control of the PGA gain to make full use of the measurement range of the ADC.

Figure 12:
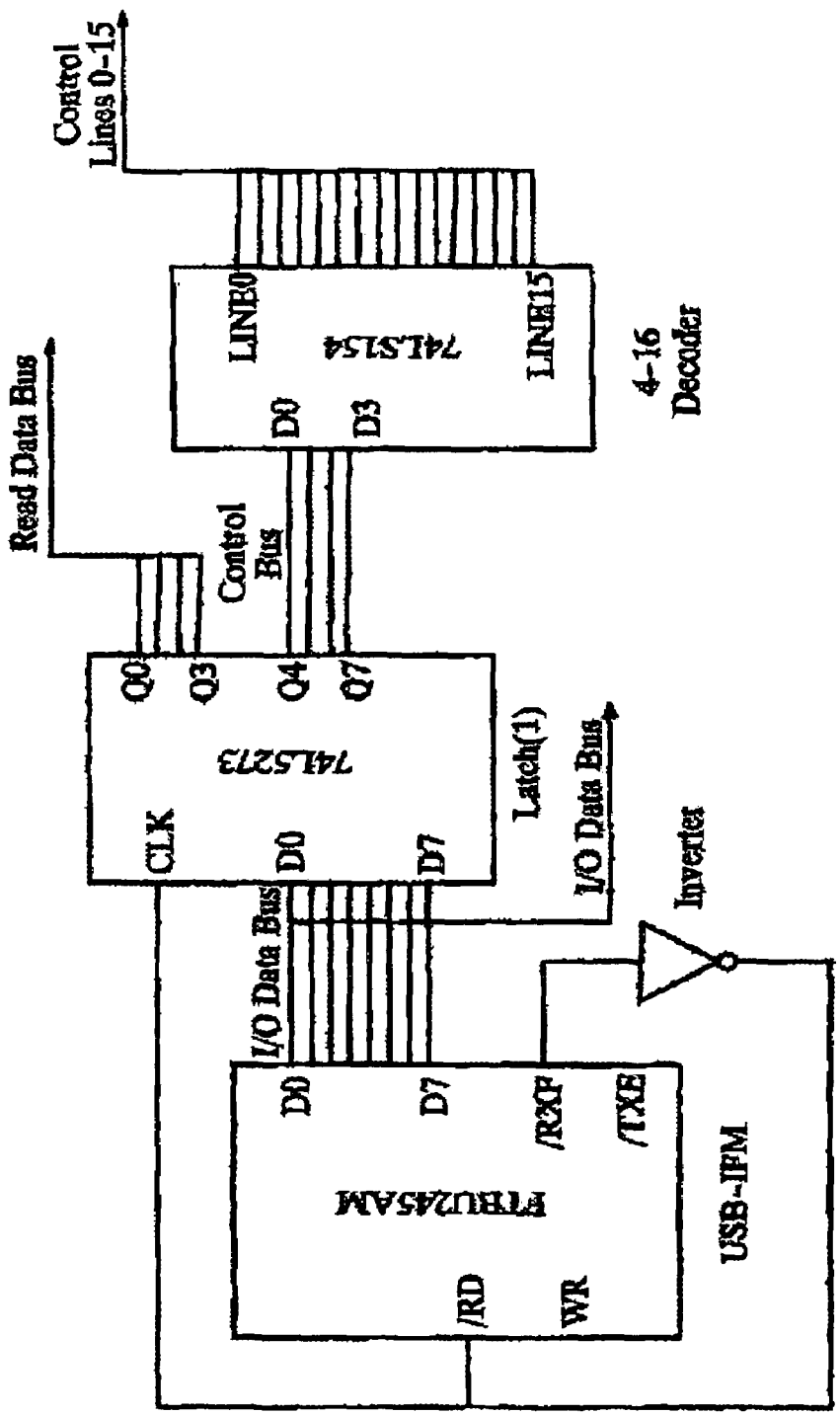
FIG. 12 is a diagram of a USB-IFM logic interface circuit.

The basic logic circuit for interfacing the USB-IFM to the electronic units in the data acquisition system is shown in FIG. 12. This circuit enables the PC 20 to select any unit and to transmit data to or receive data from any unit.

The USB-IFM output RXF# is connected to the RD# input via an inverter. The 8-bit I/O port (D0–D7) of the USB-IFM is taken to Latch (1) (74LS273), which is activated when the RD# signal goes high. The output of Latch (1) is divided into two parts, bits D0–D3 as a 4-bit Read Data Bus for all electronic units, and bits D4–D7 as a Control Bus to be taken to a 4-16 decoder chip (74LS154), whose 16 outputs are used as Control Lines to select individual units.

The operation is as follows: Initially the USB-IFM Receive Buffer is empty and so the output RXF# is "1" and RD# is "0". The PC 20 sends a data byte to the USB-IFM Receive Buffer and RXF# is automatically set to "0". After a short delay, RD# and CLK of Latch (1) become "1" via the inverter. The data byte is latched into the Latch (1) and this also causes RXF# to become "1", indicating no more data is available to be read, which in turn sets RD# to low after short delay. The system is now ready to receive more data from the PC 20 or to transmit data to the PC 20.

The PC 20 receives data one byte at a time from the USB-IFM Transmit Buffer using the instruction FT_Read. Similarly, it transmits data to the USB-IFM Receive Buffer one byte at a time using instruction FT_Write. Any data byte received by the USB-IFM is divided by the logic circuit into two parts, the 4 least significant bits (LSBs) and the Read Data Bus and the 4 most significant bits (MSBs) as the Control Bus.

The Control Bus is taken to the 4-16 decoder to select one of 16 Control Lines, which activate 16 different ICs in the data acquisition and measurement circuits as listed in Table 1.

TABLE 1

Control line connections

| Control | Activated unit | Board location |
| --- | --- | --- |
| 0 | Data acquisition | Data acquisition card |
| 1 | Data acquisition | Data acquisition card |
| 2 | Data acquisition | Data acquisition card |
| 3 | DAC | Data acquisition card |
| 4 | MUX + DC PGA | Data acquisition card |
| 5 | ADC | Data acquisition card |
| 6 | Measurement | Measurement channel |
| 7 | Measurement | Measurement channel |
| 8 | Measurement | Measurement channel |
| 9 | DDS Latch (1) | Signal generator PCB |
| 10 | DDS Latch (2) | Signal generator PCB |
| 11 | Measurement | Measurement channel |
| 12 | Measurement | Measurement channel |
| 13 | Measurement | Measurement channel |

TABLE 1-continued

Control line connections

| Control | Activated unit | Board location |
|---|---|---|
| 14 | Measurement Latch (2) | Measurement channel PCB (2) |
| 15 | Measurement | Measurement channel |

Figure 13:
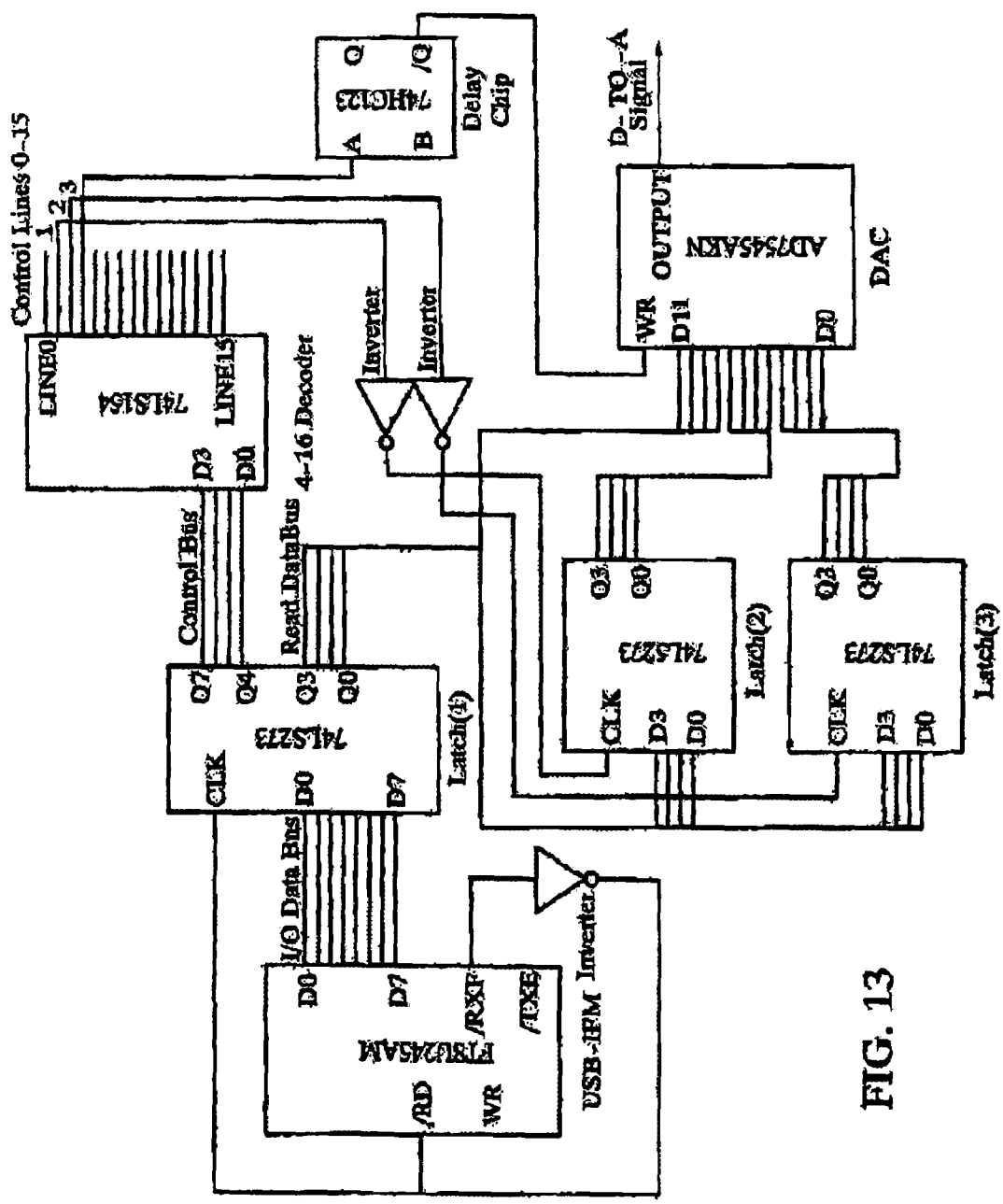
FIG. 13 is a diagram of interfacing USB-IFM to DAC.

The full logic circuit for interfacing the USB-IFM to the DAC 34 is shown in FIG. 13. The 4-bit Read Data Bus and 3 Control Lines of the basic USB logic interface circuit (see FIG. 12) are used. The main consideration is to supply the 12-bit data input from the 4-bit Read Data Bus.

The 4-bit Read Data Bus is extended to give a 12-bit input signal to the DAC 34 by two additional latches, Latch (2) and Latch (3). The 4-bit Read Data Bus is connected directly to input bus D8–D11 of the DAC 34, to Latch (2), whose outputs go to input bus D4–D7, and to Latch (3), whose outputs go to input bus D0–D3. A mono-stable chip (74HC123) is inserted in the Control Line (3) to ensure that the control signal width is adjusted to correct DAC operation. Control Lines 1, 2 and 3 activate Latches (2) and (3) and the DAC 34 respectively.

The method of loading a 12-bit signal into the DAC 34 is as follows: The PC 20 sends a byte containing bits D0–D3 of the signal plus binary 2 (the Control Line for Latch (3)). Latch (3) is activated and bits D0–D3 appear at the corresponding inputs of the DAC 34. The PC 20 sends a second byte containing bits D4–D7 of the signal plus binary 1 (the Control Line for Latch (2)). Latch (2) is activated and bits D4–D7 appear at the corresponding inputs of the DAC 34. The PC 20 sends a third byte containing bits D8–D11 of the signal and binary 3 (the Control Line for the DAC). Bits D8–D11 of the signal appear at the corresponding inputs of the DAC so that the complete 12-bit signal now appears at the DAC inputs bus. The Control Line (3) signal now locks out the DAC inputs, so that the analogue output is held at the value sent by the PC 20.

The first FT_Write instruction sends data bits D0–D3 to Latch (3) and the second instruction sends data bits D4–D7 to Latch (2). The third instruction sends the data bits D8–D11 and activates the DAC 34 with the complete data bits D0–D11. The final instruction does not activate a unit, but is used to reset the active Control Line to "1". It is used after all operations. The DAC operation is summarized in Table 2.

TABLE 2

DAC Operation

| USB-IFM | Activated | Control | Read data |
|---|---|---|---|
| FT_Write | Latch (3) | 2 | Bits 0–3 |
| FT_Write | Latch (2) | 1 | Bits 4–7 |
| FT_Write | DAC | 3 | Bits 8–11 |
| FT_Write | (Reset) | 8 | Any data |

Figure 14:
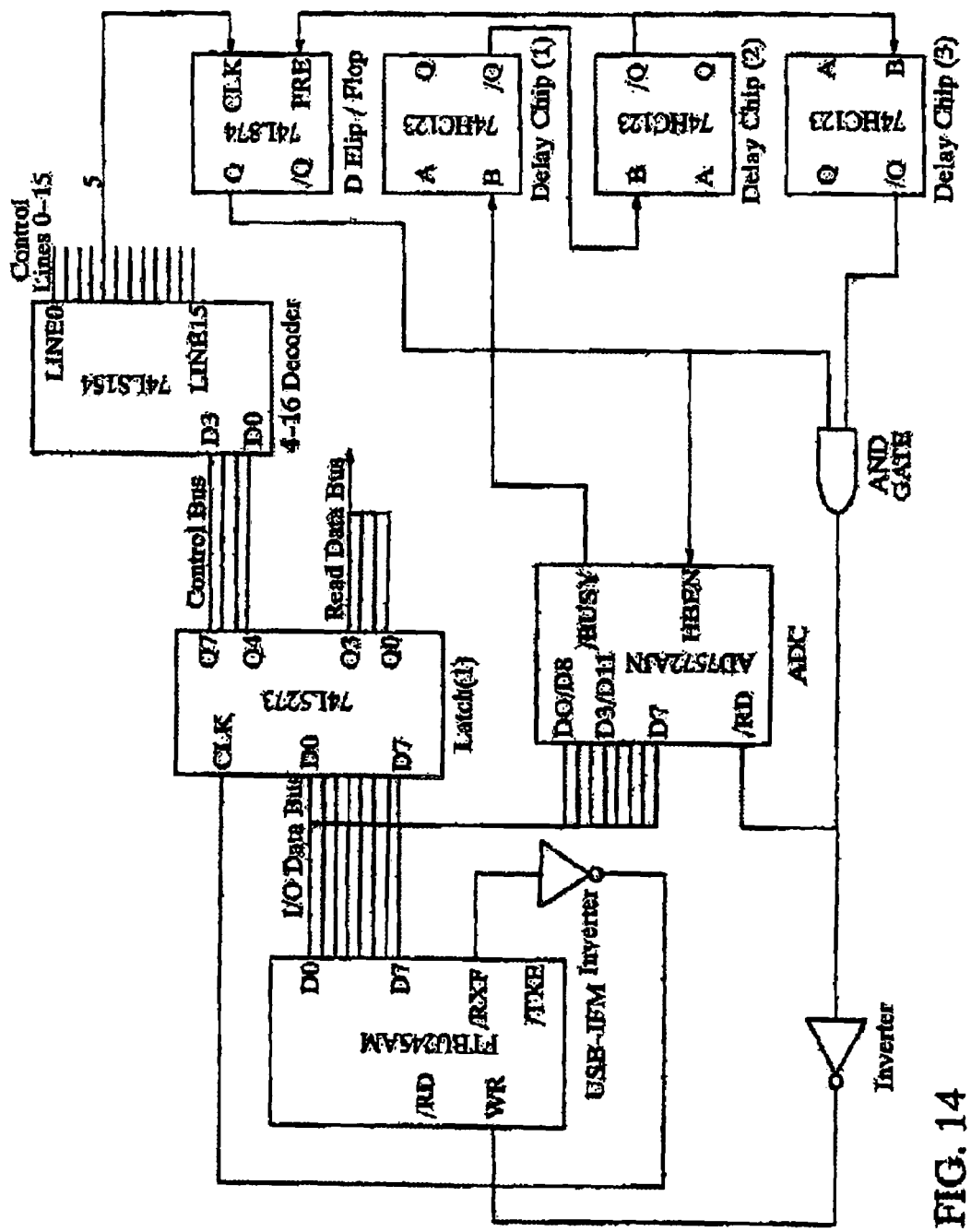
FIG. 14 is a diagram of interfacing USB-IFM to ADC.
Figure 15:
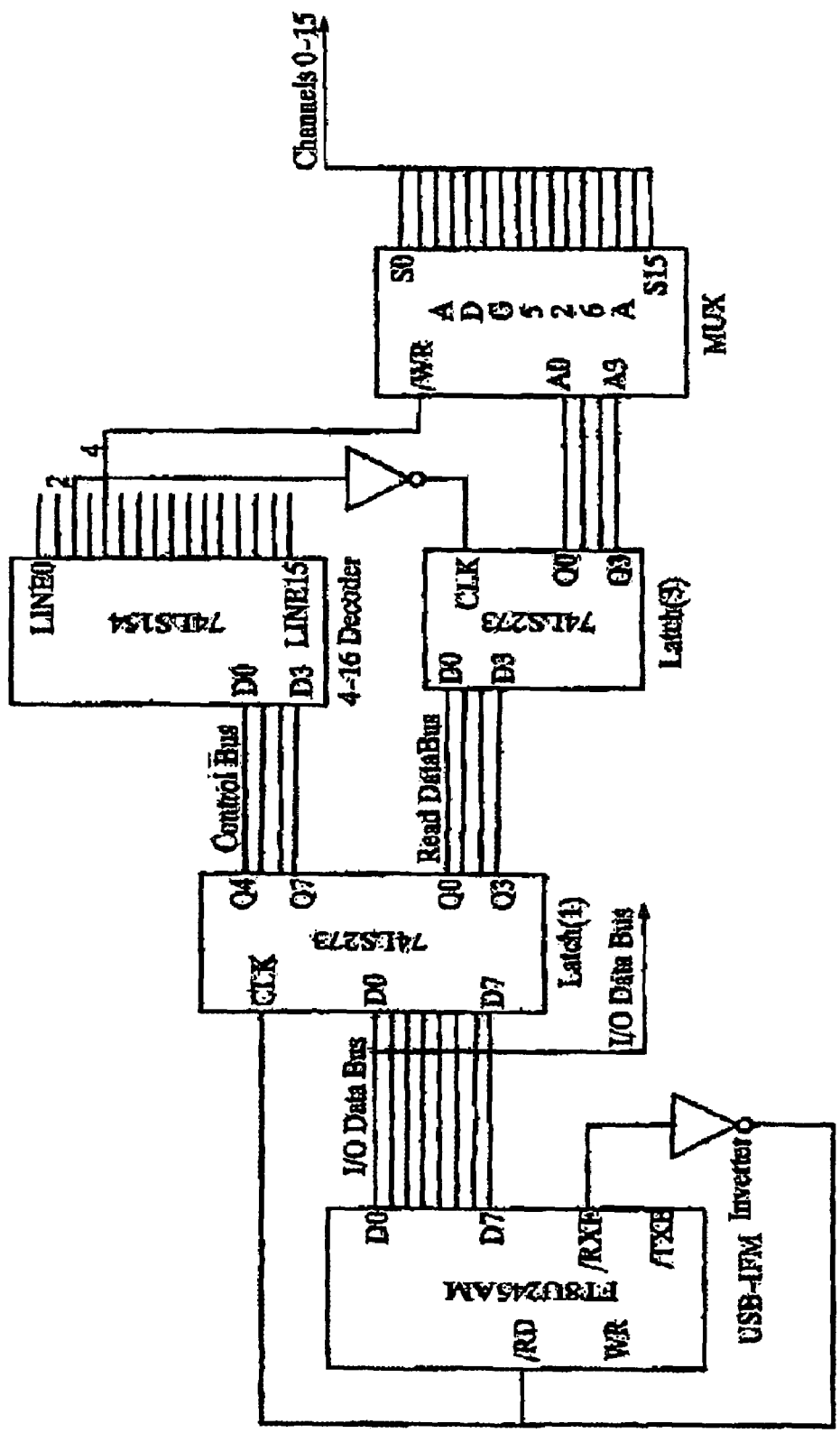
FIG. 15 is a diagram of interfacing USB-IFM to MUX.
Figure 16:
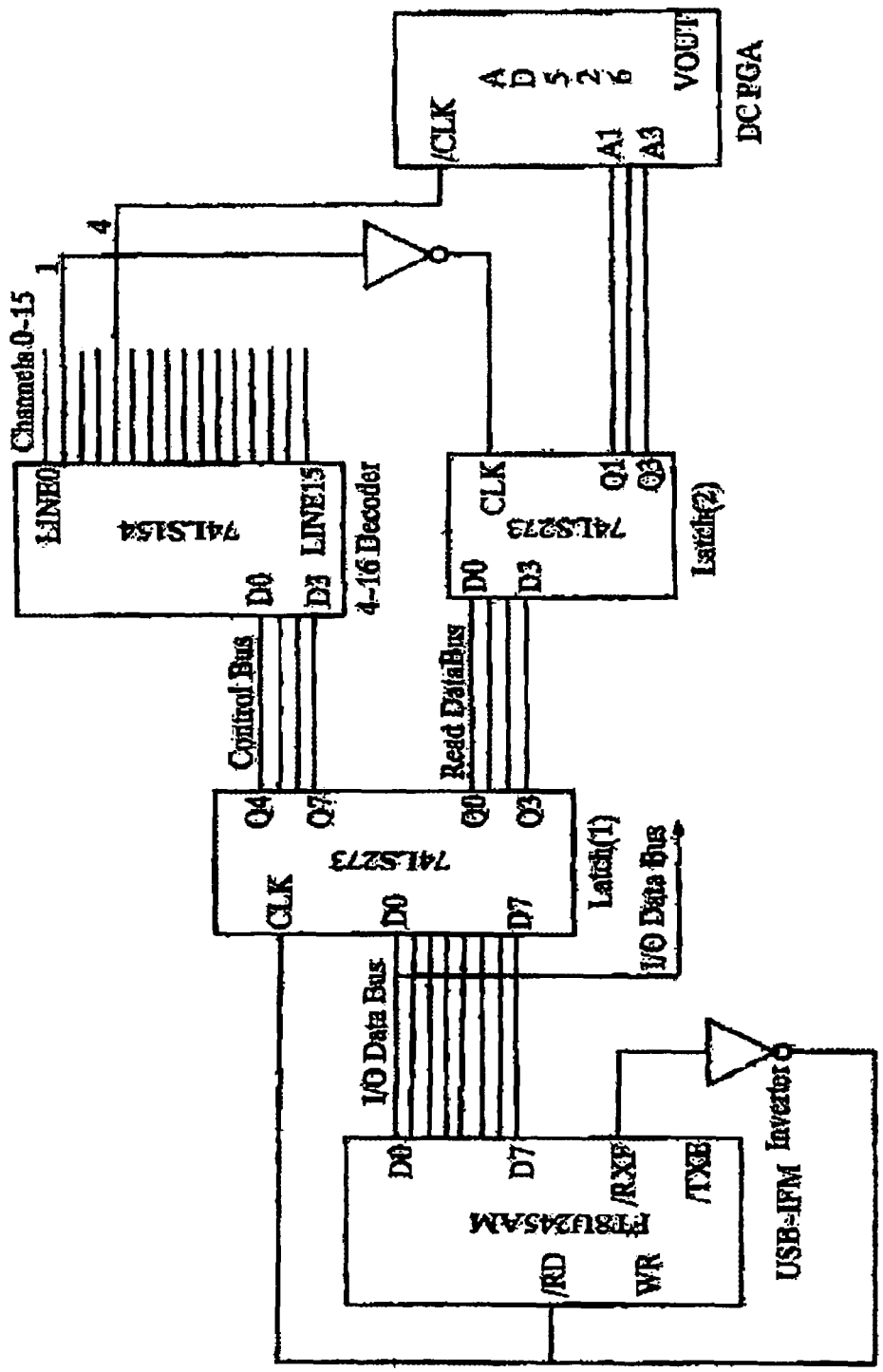
FIG. 16 is a diagram of interfacing USB-IFM to DC PGA.

The full logic circuit design for interfacing the USB-IFM to the ADC is shown in FIG. 14. The 8-bit I/O Data Bus and Control Line (5) of the basic USB logic interface circuit (FIG. 12) are used. The 8 ADC output data lines D0–D3 (or D8–D11) and D4–D7 are connected to the 8-bit I/O Data Bus. The Control Line (5) is taken to the /RD input of the ADC via a D flip-flop (74LS74) and an AND gate.

The method of obtaining the 12-bit signal from the ADC is as follows: The PC 20 send a byte to the USB-IFM containing binary 5 (the Control Line for the ADC) to activate the ADC conversion and the /BUSY signal goes low. At the end of conversion /BUSY goes high new data DB0–DB7 appear on the output lines of the ADC (since HBEN is low) and a sequence of three delay timers) is initiated by using 3 delay chips (74HC123). After the first delay a WR signal is generated, which writes data DB0–DB7 into the USB-IFM Transmit Buffer. After the second delay HBEN is set high, the data DB8–DB11 plus 4 zeros appear on the ADC data output. After the third delay a second WR signal is generated, which writes this data DB8–DB11 into the USB-IFM Transmit Buffer. The PC 20 can now read the ADC conversion result from the USB-IFM Transmit Buffer in two bytes. The FT_Write instruction activates the ADC and also sends the result as two bytes to the USB-IFM Transmit Buffer via the logic circuits. The FT_Read instructions send these two bytes to the PC 20. They do not activate any unit or put any data on the Read Data Bus. The ADC operation is summarized in Table 3.

TABLE 3

ADC operation

| USB-IFM | Activated | Control | Read data |
|---|---|---|---|
| FT_Write | ADC | 5 | Any data |
| FT_Write | (Reset) | 8 | Any data |
| FT_Write | USB-IFM | X | X |
| FT_Write | USB-IFM | X | X |

Figure 8:
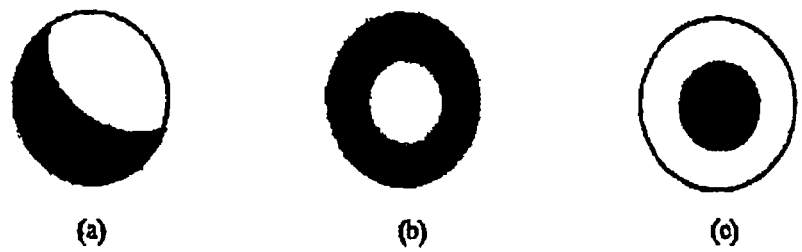
FIG. 8a is an image of a stratified distribution.
FIG. 8b is an image of a core distribution.
FIG. 8c is an image of an annular distribution.

The full logic circuit design for interfacing the USB-IFM to the MUX is shown in FIG. 8. The 4-bit Read Data Bus and two Control Lines of the basic USB logic interface circuit (FIG. 5) are used. The 4-bit Read Data Bus is connected to Latch (3), whose outputs go to the input bus A0–A3 of the MUX. Control Lines (2) and (4) activate Latch (3) and the MUX respectively.

The method of operating the MUX is as follows: The PC 20 sends a byte to the USB-IFM containing binary 2 (the Control Line for Latch (3)). Latch (3) is activated and the Read Data Bus data appear at the corresponding inputs of the MUX. The PC 20 sends a second byte to the USB-IFM containing binary 4 (the control line for the MUX). The MUX is activated, whose outputs select one channel according to the 4-bit Read Data Bus data.

The full logic circuit design for interfacing the USB-IFM to the DC PGA is shown in FIG. 9. The 4-bit Read Data Bus and two Control Lines of the basic USB logic interface circuit (FIG. 5) are used. The 4-bit Read Data Bus is connected to Latch (2), whose last three outputs go to input bus A1–A3 of the DC PGA. The Control Lines (1) and (4) activate Latch (2) and the DC PGA, respectively.

The method of operating the DC PGA is as follows: The PC 20 sends a byte to the USB-IFM containing binary 1 (the Control Line for Latch (2)). Latch (2) is activated and the Read Data Bus data appear at the corresponding inputs of the DC PGA. The PC 20 sends a second byte to the USB-IFM containing binary 4 (the Control Line for the DC PGA). The DC PGA is activated, whose outputs select a gain according to the last 3-bit Read data Bus data. Note that the Control Line (4) activates both the MUX and the DC PGA. The operation of the UX and the DC PGA is summarized in Table 4.

TABLE 4

MUX and DC PGA operation

| USB-IFM | Activated | Control | Read data |
|---|---|---|---|
| FT_Write | Latch (3) | 2 | Bits 0–3 MUX |
| FT_Write | Latch (2) | 1 | Bits 1–3 DC |
| FT_Write | DC PGA and | 4 | Any data |
| FT_Write | (Reset) | 8 | Any data |

The first instruction sends data bits D0–D3 to the 4 input channel select bits of the MUX via Latch (3). The second instruction sends data bits D1–D3 to the 3 gain select bits of the DC PGA via Latch (2). The third instruction activates both the MUX and the DC PGA.

Figure 17:
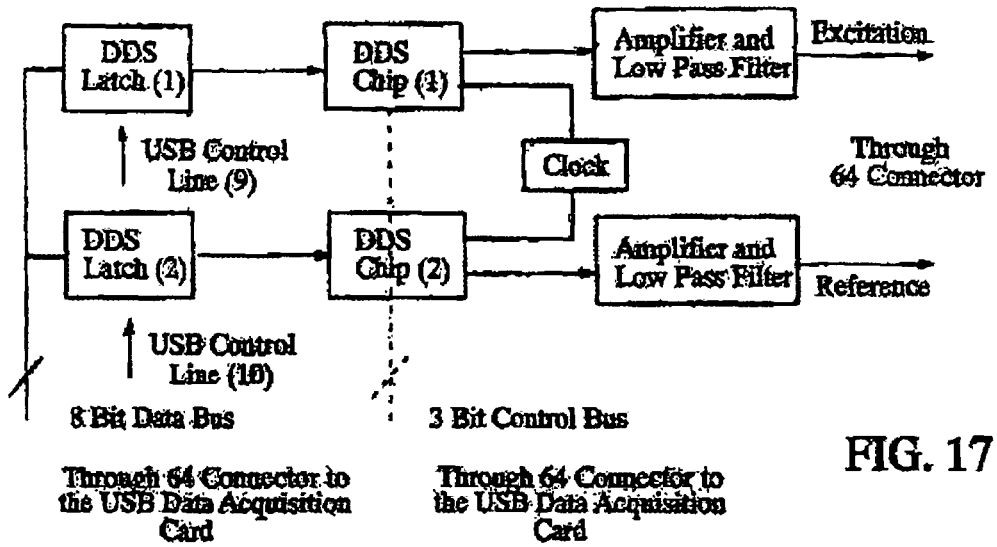
FIG. 17 is a diagram of a DDS signal generator board.

The DDS chip AD7008 is a complex device and its control is more complicated than other units in the data acquisition system. A schematic diagram of the DDS signal generator board controlled by the USB data acquisition card is shown in FIG. 17.

The frequency, amplitude and phase of the DDS output sine wave are set by 3 internal registers, which must be loaded externally via the data inputs (D0 and D7) and a Parallel Assembly Register. The data inputs (D0–D7) of the DDS chips are supplied via the DDS latches. The input to these latches comes from data lines on the USB and data acquisition card (4 bit Read Data Bus plus Latch (3)). The 4 LSBs of the DDS latch outputs are also connected to the DDS transfer logic inputs TC0–TC3. Once data has been written into the Parallel Assembly Register, these bits can be loaded into the appropriate internal register, according to the contents of TC0–TC3.

Control Lines (9) and (10) from the USB data acquisition card are used to set the DDS latches, but the control signals for the two DDS chips (i.e. RESET, /WR, and LOAD) are taken from the USB data acquisition card data lines to latch (4)(bits 8 to 10).

The operation to set up the two DDS chips involves sending data to each chip via its individual latch and setting the 3 DDS control inputs via Latch (4) (on the USB data acquisition card) as listed in Tables 5 and 6.

All control signals to AD7008 are connected to Latch (4) of the USB data acquisition card via a 64-connector. When the AD7008 is operated, the Control Bus is set to "0" and the Read Data Bus is set to activate the appropriate control input.

The data lines of AD7008 are controlled by the USB data acquisition card through two latches DDS Latch (1) and DDS Latch (2). The first FT_Write instruction sends data bits D0–D3 to latch (3) of the USB data acquisition card. The second instruction sends data bits D4–D7 and activates one of the DDS latches with the complete data bits D0–D7.

TABLE 5

Control lines operations of AD7008

| USB-IFM | Activated unit | Control | Read data bus |
|---|---|---|---|
| FT_Write | Data acquisition | 0 | 3 (0011 activating |
| FT_Write | Data acquisition | 0 | 0 (0000) activating |
| FT_Write | Data acquisition | 0 | 6 (0110) activating |

TABLE 6

Data lines operation of AD7008

| USB-IFM | Activated unit | Control | Read data bus |
|---|---|---|---|
| FT_Write | Data acquisition | 2 | Bits 0–3 for DDS |
| FT_Write | DDS Latch (1) | 9 | Bits 4–7 for DDS |
| FT_Write | DDS Latch (2) | 10 | Bits 4–7 for DDS |
| FT_Write | Reset | 8 | Any data |

Figure 18:
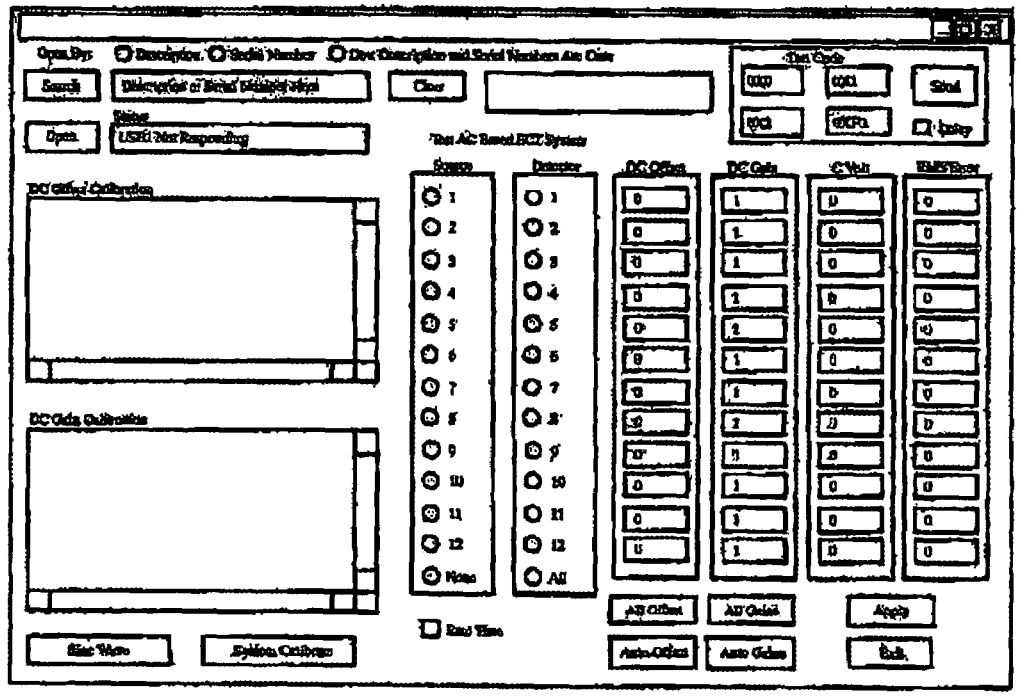
FIG. 18 is a diagram of a Windows user interface.

The software for the USB data acquisition card was written in Visual C++6.0, which is convenient for interfacing peripheral devices, display and design of user interface. FIG. 18 shows the Windows user interface.

It has following functions:

(1) Control of the signal generator board;

(2) Management of the menu and setting of the system parameter and initialization of the system;

(3) Control of the capacitance measurement boards and acquisition of the capacitance data;

(4) Control of the DAC and ADC to obtain the automatic DC offsets and gains functions; and (5) Real-time data acquisition.

From the foregoing, it should be readily apparent that the method and apparatus provides a high-speed USB data acquisition card for the ECT system. The electronic circuits have been designed and a PCB has been made complying with the Eurocase and Eurocard standards. The card can support up to 12 capacitance measurement channels and has been successfully incorporated into the system. The software includes automatic calibration for obtaining the DC offsets to cancel the standing capacitance and the DC amplifier gain settings, and the collection of the measurement data for image reconstruction and analysis, together with a user friendly Windows (trademark) interface.

As noted above, computer 20 may assume various configurations depending upon the specific application. For example, a portable laptop computer may be employed for certain applications such as checking luggage left unattended in an airport lobby. For other applications, the personal computer 20, may be used as a stand alone system, a work station and file server in a local area network or in a wide area network over the Internet.

Figure 3:
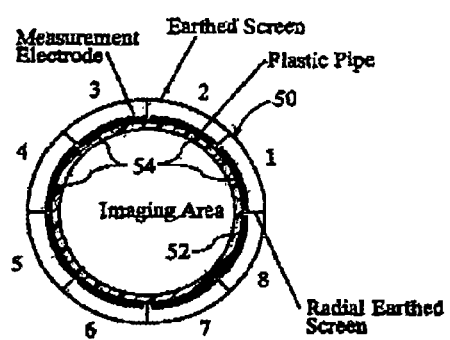
FIG. 3 is a cross-sectional view taken substantially along lines 3—3 of FIG. 1.

The transducer 50 illustrated in FIGS. 1 and 3 of the drawings includes a plastic cylinder or pipe 52 having eight electrodes 54 positioned around the periphery of the cylinder. A similar electrical capacitance tomography (ECT) transducer is described and illustrated in British Patent No. GB 2,329,476 to Wu Quiang Yang entitled "Image Creation in a Tomography System," the disclosure of which is incorporated herein by reference. The patent describes use of the device for taking a series of measurements of capacitance across a conduit obtained by exciting electrodes 54 positioned around an outer wall of the conduit 52. The capacitance measurements are used to construct an image of a section through the conduit 52 which represents the relative proportions and location of dielectric materials within the conduit 52. The patent describes a method for creating an image representing internal properties of a region from measurements of electrical parameters at the perimeter of the region, in combination with image correction data derived from an iterative feed back algorithm which runs quickly on a "Pentium computer."

Several patents issued to Kathleen Hennessey disclose image databases and knowledge databases which have been used heretofore for detecting imperfections in printed circuit boards. These patents include U.S. Pat. No. 5,515,453; U.S. Pat. No. 5,553,168; U.S. Pat. No. 5,703,969; U.S. Pat. No. 6,014,461; U.S. Pat. No. 6,091,846; U.S. Pat. No. 6,205,239; U.S. Pat. No. 6,246,787 and U.S. Pat. No. 6,246,788, the disclosures of which are incorporated herein by reference.

As will be hereinafter more fully explained, back propagation is used to provide supervised learning for building image and knowledge based databases wherein error data is back propagated to earlier ones for allowing incoming weights to be updated. Image indexing and searching based on image primitives may be used for creating 3D real-time images of concealed items.

It is important to note that you do not have to produce an image of an object to detect a dangerous object. The transducer signals can be used not only to detect gradients characteristic of the edge of an object, but also to detect and characterize differentiation among materials with adjacent objects. Generation of an image may only be necessary to provide human operators with visual information after the initial tomographic screening. Objects and their characteristics can be represented in symbolic hyperspace, beyond the dimensions available to visual representation methods.

In a further development of methods described in U.S. Pat. No. 5,515,453, measurement of signals obtained from said panel of sensors/transducers are used to delineate the edges of objects and to characterize the outer shape and texture of materials within said objects. In a similar manner to that by which semiconductor defects are characterized in U.S. Pat. Nos. 6,014,461, 6,091,846 and 6,205,239, a set of selected examples of dangerous objects is used to generate a Dangerous Objects Knowledgebase.

The characteristics of each example of an object to be used to generate Rules about Dangerous Objects in a Dangerous Object Knowledgebase are obtained by the following Steps 1–7.

Step 1. Whereby sets of primitives are generated from the values of transducer signals that represent either (1) a discontinuity in intensity characteristic of segments of an edge of an object or (2) a range of values of adjacent transducer signals characteristic of one or more textures of the internal materials of an object;

Step 2. Whereby sets of higher-level primitives are generated by association of several primitives to one another based on their spatial proximity and similarity of primitive values, so as to represent segments of edges and internal materials of said object by means of values of their attributes such as relative positions, sharpness, width, curvature and other characteristics derived from said transducer signals;

Step 3. Whereby said higher-level primitives are joined based on shared characteristics such as similarity of edges and internal materials to define the object;

Step 4. Whereby a set of values of descriptors of said object such as object size, curvature and sharpness of its edges, metallic texture, unique chemical texture such as of nitrates, etc. are generated from said shared characteristics as shown in Table 7 below:

TABLE 7

Characterization of Dangerous Objects

| Object ID | 2D cross section | 3D cubic volume | Edge sharpness* | Object* Eccentricity 0 = circle 100 = worm | Edge curvature* | Inner texture* coefficent | Inner texture* variability |
|---|---|---|---|---|---|---|---|
| Knife1 | 104 | 223 | 93 | 64 | 16 | −48[1] | 17 |
| Knife2 | 108 | 231 | 87 | 71 | 19 | −41[1] | 12 |
| Mine1 | 52 | 304 | 21 | 6 | 91 | 53 | 22 |
| Mine2 | 48 | 291 | 24 | 8 | 93 | 49 | 18 |
| Shaver1 | 60 | 312 | 33 | 23 | 18 | 51 | 28 |
| Shaver2 | 64 | 303 | 37 | 28 | 22 | 15 | 16 |

Figure 24A:
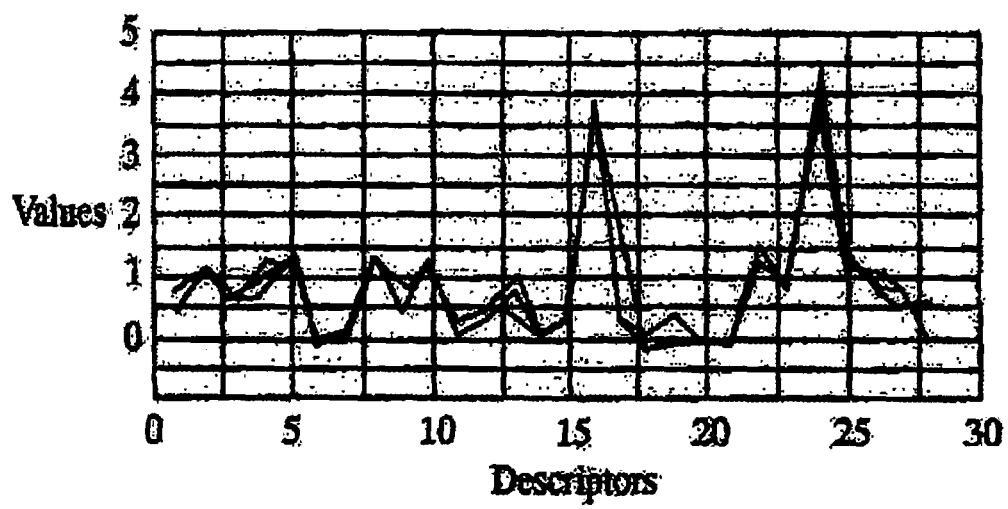
FIG. 24a is a graph showing the alignment of descriptor values of similar objects.
Figure 24B:
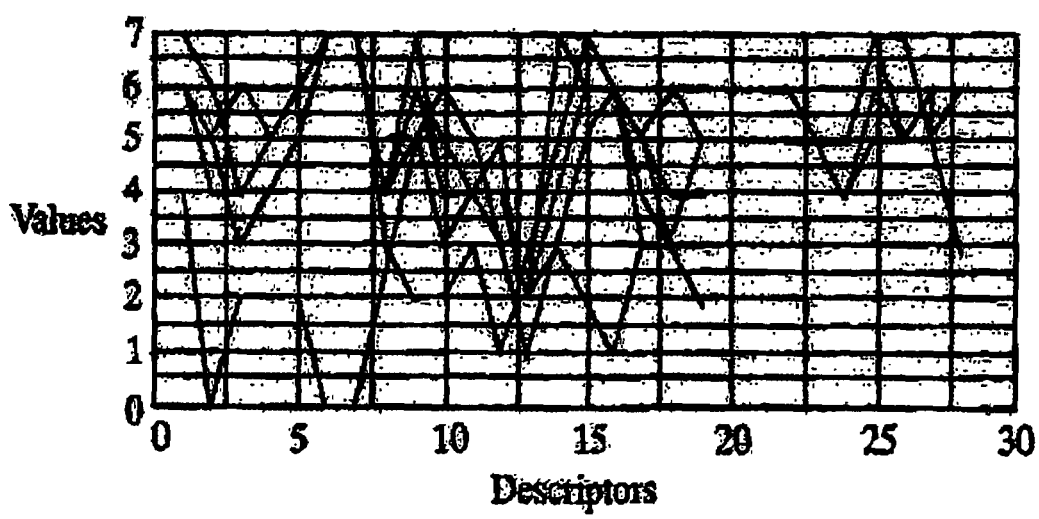
FIG. 24b is a graph showing divergence of descriptor values among dissimilar objects.

*normalized, 0–100
[1]Metals exhibit negative capacitance
[2]Shaver1 contains explosive, Shaver2 does not Step 5. Whereby Steps 1–4 are repeated with at least three and usually not more than five other similar dangerous objects whose characteristic similarity is illustrated in the graph in FIG. 24a in contrast to dissimilar objects whose divergent characteristics are illustrated in FIG. 24b;

Step 6. Whereby weights are assigned to said descriptors, so that greater weight is given to descriptors with a similar and limited range of values and lesser or no weight is given to descriptors with dissimilar or widely varying ranges of values as shown in Table 8 below:

TABLE 8

Weights Assigned to Characteristics of Dangerous Object

| Object ID | 2D cross section area | 3D cubic volume | Edge sharpness | Object Eccentricity | Edge curvature | Inner texture coefficient | Inner texture variability |
|---|---|---|---|---|---|---|---|
| Knife | 11 | 14 | 94 | 61 | 16 | 11 | 18 |
| Mine | 32 | 28 | 6 | 44 | 42 | 91 | 23 |
| Shaver w | 6 | 14 | 23 | 14 | 18 | 88 | 11 |

Step 7. Whereby the sets of values of descriptors for each group of Dangerous Objects are reduced to a single set of descriptor value midpoints and weights, each such set to be stored as a Rule in a Dangerous Objects Knowledgebase as shown in Table 9 below:

TABLE 9

Dangerous Objects Knowledgebase: attribute value midpoints and weights

| Rule | 2D cross section area | | 3D cubic volume | | Edge sharpness | | Object Eccentricity | | Edge curvature | | Inner texture coefficient | | Inner texture variability | |
|---|---|---|---|---|---|---|---|---|---|---|---|---|---|---|
| | MPt | Wt | MPt | Wt | Mpt | Wt | Mpt | Wt | Mpt | Wt | Mpt | Wt | Mpt | Wt |
| Knife | 106 | 11 | 227 | 14 | 93 | 94 | 64 | 61 | 16 | 16 | −48 | 11 | 17 | 18 |
| Mine | 50 | 32 | 298 | 28 | 22 | 6 | 7 | 44 | 92 | 42 | 51 | 91 | 20 | 23 |
| Shaver W | 63 | 6 | 307 | 14 | 35 | 23 | 26 | 14 | 20 | 18 | 38 | 88 | 22 | 11 |

Distribution, use, maintenance and specific application refinement of said Dangerous Objects Knowledgebase is described in Steps 8–12 below.

Step 8. Once the Dangerous Objects Knowledgebase is populated with Rules about Dangerous Objects that reflect accumulated relevant information about a wide variety of objects, characteristics and their relative importance, it can be used to detect and classify potentially dangerous objects in enclosed areas such as within packages and luggage by following Steps 1–4.

Step 9. The Dangerous Objects Knowledgebase, normally not larger than 15,000 bytes in size, is distributed by any electronic means to a security unit for use with a specific embodiment of the Scanning Device.

Step 10. Amendment of the Dangerous Objects Knowledgebase is achieved by addition, deletion or replacement of one or more instances of objects, so that the set of Rules in the Dangerous Objects Knowledgebase is reformulated, a process that normally takes only a few minutes and can easily be reversed.

Step 11. A master set of a Dangerous Objects Knowledgebase is created and amended on similar apparatus in locations remote from the inspection sites, and transmitted electronically to any location, providing the latest rules about dangerous objects throughout the security network.

Step 12. Several versions of a Dangerous Objects Knowledgebase may be created and maintained for different security tasks, such as one for freight and checked baggage compiled to detect explosives and accelerants and another version of the Dangerous Objects Knowledgebase for carry-on items to which would be added rules for detection of sharp metal objects such as knives.

Several embodiments of transducers which may be used separately or in combination are illustrated in FIGS. 4, 5, 6 and 19–23 of the drawings.

Four security scanning devices are described below as embodiments: (1) 3D capacitive scanner with parallel sensor arrays, (2) shoe scanner with planar capacitance sensor array, (3) magnetic scanner with planar Hall-effect sensor array and (4) multi-plane ECT for 3D imaging of metal objects and chemical substances.

Embodiment 1

3D Capacitive Scanner with Parallel Sensor Arrays

Figure 19:
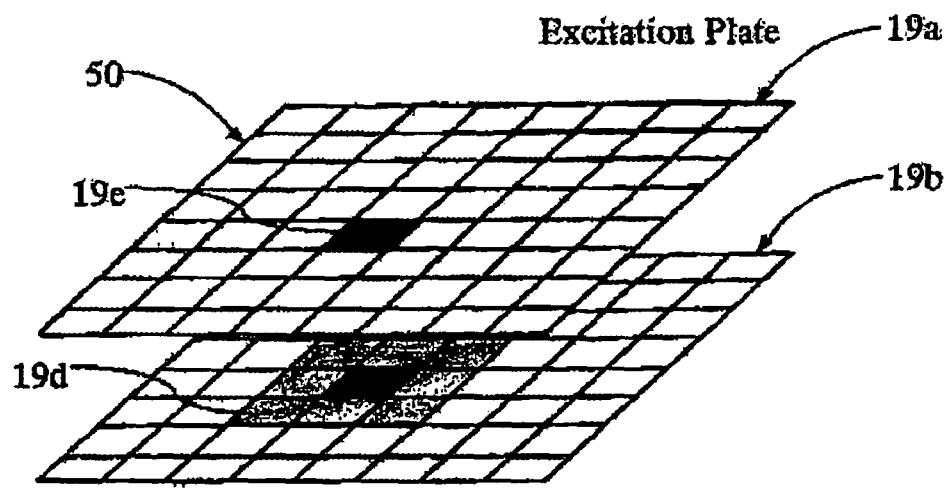
FIG. 19 is a diagrammatic view of two parallel plates, one for excitation and the other for detection, with capacitance sensor arrays on each plate.

A conventional ECT sensor consists of a number of electrodes, surrounding a cross section. An alternative design may be to use two parallel plates, one for excitation and the other for detection, with capacitance sensor arrays and say 256 (or any other number of) electrodes (say 1×1 cm or any size) on each plate. As shown in FIG. 19, when one electrode 19e is energized on the top plate 19a, say 25 capacitance measurements may be taken from the bottom plate 19b. The excitation electrodes on the top plate may be energized in turn and say over 1000 capacitance measurements may be collected from the detection electrodes on the bottom plate. To obtain the sensitivity distributions (Yang et al. 1999), a finite difference method may be used, which is more convenient than a finite element method (FEM), because of the shape of the sensing space. Each electrode may be divided into say 3×3=9 (or any other number of) pixels. The space between the excitation plate and the detection plate may be divided in software into multiple layers, so that the thickness of each layer is similar to the dimension of the pixels. In this way, the sensing space may be divided into many small cubes. This enables true 3D image reconstruction, and excellent spatial resolution may be achieved.

Both capacitance and loss-conductance components may be measured with different frequencies and different phases. The measuring circuit may be based on an AC-based ECT system design, which employs sine-wave excitation and phase-sensitive demodulation (Yang and York 1999). To measure the capacitance component, a high-frequency excitation signal (say 1 MHz) may be applied to one or more excitation electrodes for the optimized sensing field and the quadrature-phase signals may be measured from the detection electrodes by means of phase-sensitive demodulation. To measure the loss-conductance component, a low-frequency signal (say 10 kHz) may be applied and the in-phase signals may be measured. The measurement protocol may be optimized to obtain data sets with the best attributes for image resolution (Polydorides and McCann 2002). To achieve real-time imaging, parallel data acquisition channels may be used.

Many dangerous objects, such as guns and knives (metal or ceramic), may be uniquely characterized by shape alone. Others, such as explosives, may be identified by the unique electrical characteristics of the materials. On the other hand, some innocuous objects may trigger a false positive alarm because they have a suspicious shape, such as a set of wires, or because of the suspicious nature of their materials, such as hairspray. Elimination of false positive alarms is essential to the adoption of any automated inspection or scanning technology. The ability of knowledge-based image analysis to characterize objects, not only by shape but also by electrical characteristics of their materials, may substantially reduce false positive alarms, as its application in semiconductor wafer inspection has demonstrated (Lin 2001, Pham 2002).

In order to make maximum use of the information available from the tomography sensor, the capacitance and loss conductance data may be processed or extracted as sets of features, which may be represented in such a way that the information may be integrated seamlessly with other information, such as images, shapes, textures and characteristics of materials, and then may be stored in a database. By this means, the data from the sensor may be assigned to relevant characteristics of an object, so as to enable the system to extract, formulate and use rules derived from the associated data. The capacitance and loss conductance data may now become part of a dynamic knowledge base about objects and their characteristics, associated with the similarity of capacitance and loss conductance profiles.

The development of this device may involve acquisition of raw image data, noise filtering and feature extraction. For this purpose, software and hardware facilities for the knowledge-based functions may be needed. Also, information for evaluation of performance of each of the image generation technologies with regard to capabilities for shape delineation, object construction and feedback may be provided. The development of this device may also involve acquisition of knowledge-based characterization of full 3D images of dangerous objects, as well as extensive field tests to ensure acceptable system performance at the point of use. The knowledge base may provide feedback to the ECT system, in the manner of an auto-focus facility, to allow the system to optimise performance in image generation by different measurement protocols and different excitation frequencies. By means of the image knowledge-base technology, real-time image analysis may be achieved, including detection and identification of dangerous objects.

This device may be used to check, but not limited to, briefcases in airports and envelopes and/or small parcels in post offices and parcel delivery services. An object may be placed in between the two plates. If a metal or ceramic knife or explosive material is inside, the imaging system may show the contents inside as a 3D image to identify them. This device may be the first of its kind to prevent criminals from sending bombs, anthrax and other dangerous materials through airports, post offices and parcel delivery services. This device may also be used as a portable device for checking abandoned briefcases, which cause significant problems in airports.

Embodiment 2

Shoe Scanner with Planar Capacitance Sensor Array

In the past, terrorists have resorted to concealing explosives in their shoes, which is so-called "shoe-bomb". In many airports, especially in the USA, all passengers must take their shoes off for checking by security personnel. There are obviously problems with this method: (a) explosives hidden inside the sole or heel cannot be seen; (b) it is time-consuming, requiring additional staff and causing long queues, (c) the experience can be unpleasant for both airline passengers and security staff.

It has been indicated experimentally that using a capacitance sensor array, a 2D image may be generated to show a plastic or metal object buried in sand. It has been shown that with a capacitance panel with a 256 sensor array, the shape of feet may be visualized and size determined.

The sensing pad as Embodiment 2 may consist of say 256 (or any number of) electrodes (similar to that shown in FIG. 19) energized in turn. When one electrode is energized, inter-electrode capacitance may be measured from say 24 (or any other number of) surrounding electrodes. Considering that excitation electrodes near the edge will not have as 24 surrounding electrodes, there may be a little less than 256×24=6144 measurements. Like Embodiment 1, sensitivity distributions may be found by finite difference simulation. Image reconstruction algorithms may be implemented for 2D and 3D display. A high image resolution may be expected, because of the measurement protocol and prior knowledge in sensitivity distribution. Like Embodiment 1, each electrode may be divided into 9 (or any other number of) pixels, giving say 2304 pixels in a 2D image and more number of cubes in a 3D image. Similar to the approach proposed for Embodiment 1, knowledge-based image analysis may be applied, in consideration of metal, ceramic, explosive and other dangerous materials. In addition to the use as a shoe scanner, a hand-held version will also be considered for other portable applications as an imaging tool, e.g., for replacing the conventional metal detector and for plastic landmine detection.

Embodiment 3

Magnetic Scanner with Planar Hall-Effect Sensor Array

Figure 20:
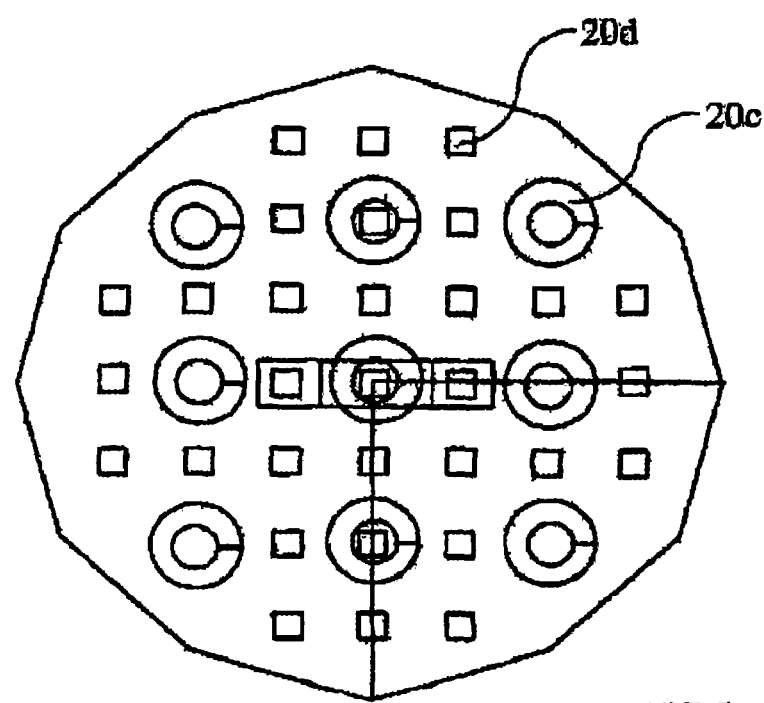
FIG. 20 is a diagrammatic view of a magnetic scanner with excitation coils and Hall-effect sensors.

While present metal detectors can only detect the presence of metal, the invented magnetic scanner may provide the information on size and/or shape of metal object(s). This sensor may consist of say 9 (or any other number of) coils $20c$, as illustrated in FIG. 20, to produce an AC magnetic field and say 28 (or any other number of) Hall-effect sensors $20d$ as detectors. The coils $20c$ may be energized in turn. When one coil $20c$ is energized, say 28 (or any other number of) measurements may be taken from the said 28 (or any other number of) Hall-effect sensors $20d$. In total say 252 measurements may be taken from the sensor. 3D sensitivity maps may be needed for image reconstruction from the said 252 measurements.

The sensor panel may consist of say 9 (or any other number of) coils to produce say 10 kHz magnetic fields and the said 28 Hall-effect sensors as detectors as shown in FIG. 2. The sensors, which may be made of say strained Indium-Gallium-Arsenide (InGaAs) hetero-structures or any other Hall-effect sensors, are small in size (say 1.5×3 mm) and offer high resolution (say 0.1 µTesla) with a large dynamic range (say up to 1 Tesla) (Haned and Missous 2003). The coils may be energized in turn. When one coil is energized, the said 28 measurements may be taken from the Hall-effect sensors. In total, say 252 measurements may be taken from the sensor panel. The data acquisition system may be similar to that used to measure capacitance, except for the transducer circuit.

To reconstruct an image from the said 252 measurements, 3D sensitivity distributions may be needed and may be calculated using a finite element software package say from Ansoft Inc. (USA). After the subject has been interrogated from many different angles, the measured data may be used to reconstruct a 2D and/or 3D image of metal object(s). This device may be designed using a PC 20 or any other types of desktop computer for data acquisition, image reconstruction, image processing and image display. A hand-held tool 60, illustrated in FIGS. 21–23 uses a microcontrooler, DSP or any other types of microprocessor, with an LCD display panel and operated by battery. It may be used by security personnel to scan people and small bags. This invented device may also be used for metal landmine detection. Again, the advantage of this device over conventional metal detectors is that it may provide images, showing the shape and/or size of metal objects and reducing false alarming. Note that the success rate of landmine detection using the conventional metal detector is as low as 0.1% (Allsopp 2000). As with Embodiments 1 and 2, knowledge-based image analysis may be applied to Embodiment 3. In the future, this device may be combined with the planar capacitance-based imaging device (Embodiment 2) to obtain enhanced images by data and image fusion.

As shown in FIGS. 21–23, the invented hand-held device preferably has a plurality of layers, which may include Layer 1: LCD display and keypad;
Layer 2: Sensing electronics and DSP;
Layer 3: Magnetic shielding;
Layer 4: Excitation coils;
Layer 5: Pre-amplifiers and MUX; and
Layer 6: Hall-effect sensors.

This invented device may be combined together with the planar capacitance imaging sensor array to obtain enhanced images.

Embodiment 4

Multi-plane ECT for 3D Imaging of Metal Objects and Chemical Substances

In the past, the ECT technology has been developed for imaging dielectric materials of different permittivities, such as gas ($\epsilon_r$=1.0) and oil ($\epsilon_r$=2.1). We have observed that metals produce extremely strong signals, representing a negative change in capacitance. Experiments demonstrated that by simply inverting the capacitance data during image reconstruction, a metal object may be seen with an existing ECT system. This indicates that an ECT system may be used as a security scanner to detect, locate and provide images of metal objects in a cross section. The key issues are improving image resolution and reliably identifying metal objects. In Embodiment 4, the sensor for 3D imaging may consist of say 4 (or any other number of) rings of capacitance electrodes, say 16 (or any other number of) electrodes in each ring. The electrodes may surround a circular or rectangular tunnel. Similar to Embodiments 1 and 2, both capacitance and loss-conductance components may be measured from the sensor arrays, in order to obtain more independent measurements so that dangerous objects or materials may be identified more reliably.

Because a metal object produces completely different changes in capacitance from dielectric materials, specific sensitivity distributions for metal objects need to be found for reconstructing images of a metal object. The loss-conductance measurements may also be used to reconstruct appropriate images. In both cases, sensitivity distributions in 3D need to be calculated, using say the Ansoft software or any other FEM or finite difference software. The two images may be integrated together by image fusion to produce a more accurate representation of metal objects.

2D images may be reconstructed from sets of measurement data from each ring of electrodes, and then say 4 images from all rings of electrodes may be stacked together to present a 3D image. For use in airports, a tunnel of say 60 cm in diameter may be designed, each ring having say 16 (or any other number of) electrodes of say 10 cm length, where a handbag may be placed inside. When the system is operated for 2½D imaging, the said 16 electrodes in each ring may provide say 120 capacitance measurements and say 120 loss-conductance measurements. Four images may be reconstructed from the capacitance data using say the Landweber iterative algorithm or any other image reconstruction algorithms (Yang et al. 1999, Yang and Peng 2003), and 4 images from the loss conductance data. Then two virtual 3D images may be constructed from the capacitance images and the loss-conductance images respectively. Finally, a 3D image may be generated by fusing the two images together. In order to obtain a true 3D image, the measurement protocol may be much more complicated than the conventional approach. In this case, when one electrode or a group of electrodes is energized, capacitance and loss-conductance measurements may be taken from all other electrodes in all the rings. There may be many more independent measurement data available from the sensor and an improved image may be expected. Similar to Embodiments 1, 2 and 3, knowledge-based image analysis may be applied to Embodiment 4.

From the foregoing, it should be apparent that:

1. Security scanning devices based on electrical tomography (more specifically ECT and EMT) and knowledge-based image analysis and understanding, each device comprising a sensing head, sensing electronics, image reconstruction and image analysis microprocessor (either microcontroller, DSP, laptop or desktop PC), a display unit and accompanying software offers significant advantages of prior devices.

2. The security scanning devices enable enhancement of image resolution with ECT and EMT. More sensors, more sensitive circuits and flexible/optimal measurement protocols may be employed for obtaining more independent measurements.

3. The security scanning devices enable implementation of data fusion to combine the complementary sensitivity of ECT and EMT (maybe together with x-ray) to different material properties.

4. The security scanning devices enable determination of optimal techniques for noise filtering, feature extraction, construction of objects, generation of their attributes, and production of feedback signals to multiple image generation units, which may utilize a variety of imaging technologies.

5. The security scanning devices provide architecture and means to implement image knowledge bases, which may characterise objects, whose image attributes are acquired from multiple sensors.

6. The security scanning devices may be operated real-time with a large number of sensors, which may need parallel measurement channels and parallel data processing.

7. The security scanning devices may provide tomographic or non-tomographic images, in 2D or 3D, of dangerous objects (such as guns and knifes, metal or ceramic) and chemical substances (such as explosive), supported by knowledge-based image analysis and understanding for identifying dangerous objects and chemical substances.

8. The security scanning devices may be used in airports, post offices and other sectors dealing with public access, such as public theatres, railway stations, government buildings, sports events and other vulnerable venues.

Terms such as "left," "right," "clockwise," "counter-clockwise," "horizontal," "vertical," "up," and "down" when used in reference to the drawings, generally refer to the orientation of the parts in the illustrated embodiment and not necessarily during use. These terms used herein are meant only to refer to relative positions and/or orientations, for convenience, and are not to be understood to be in any manner otherwise limiting.

While various embodiments and applications of this invention have been shown and described, it is obvious that modifications are possible without departing from the concepts of this invention. Therefore, the invention is not limited to described examples or embodiments.

What is claimed is:

1. A security scanning device for scanning, identifying and imaging the contents of devices in a sensing space, comprising:
   a plurality of arrays of sensor means adjacent the sensing space;
   means for developing a plurality of electric fields between at least one excitation electrode and each of a plurality of detection electrodes of a second array of detection electrodes of said sensor means in response to input signals applied to said excitation electrode of said sensor means;
   software for attributing different sensor signals for dividing the sensing space into small cubes in multiple layers;
   means for delivering signals from each detection electrode of said second array of detection electrodes of said sensor means to a data acquisition system;
   means for analyzing signals received by said data acquisition system to determine the nature of the devices in said sensing space and to image a cross-section of the device; and
   a knowledge database associated with said means for analyzing signals received by said data acquisition system, said database being indexed such that data is used for back propagation for identifying concealed objects.

2. A security scanning device for scanning, identifying and imaging the contents of devices in a sensing space, according to claim 1, said plurality of arrays of sensor means adjacent the sensing space being configured to enable implementation of data fusion to combine the complementary sensitivity of ECT and EMT to different material properties.

3. A security scanning device for scanning, identifying and imaging the contents of devices in a sensing space, according to claim 1, said means for delivering signals from each detection electrode of said second array of detection electrodes of said sensor means to a data acquisition system being configured to enable determination of optimal techniques for noise filtering, feature extraction construction of objects, generation of their attributes, and production of feedback signals to multiple image generation units, which utilize a variety of imaging technologies.

4. A security scanning device for scanning, identifying and imaging the contents of devices in a sensing space, according to claim 1, said means for analyzing signals received by said data acquisition system to determine the nature of the devices in said sensing space and to image a cross-section of the device, comprising:
   architecture and means to implement image knowledge bases, which characterize objects, whose image attributes are acquired from multiple sensors.

5. A security scanning device for scanning, identifying and imaging the contents of devices in a sensing space, according to claim 1, said plurality of arrays of sensor means adjacent the sensing space comprising:
   capacitive and inductive sensors.

6. A security scanning device for scanning, identifying and imaging the contents of devices in a sensing space, according to claim 1, said plurality of arrays of sensor means adjacent the sensing space comprising:
   capacitive sensors.

7. A security scanning device for scanning, identifying and imaging the contents of devices in a sensing space, according to claim 1, said plurality of arrays of sensor means adjacent the sensing space comprising:
   inductive sensors.

8. A security scanning device for scanning, identifying and imaging the contents of devices in a sensing space, comprising:
   a plurality of arrays of sensor means adjacent the sensing space;
   means for developing a plurality of electric fields between at least one excitation electrode and each of a plurality of detection electrodes of a second array of detection electrodes of said sensor means in response to input signals applied to said excitation electrode of said sensor means;
   means for dividing the sensing space into small cubes in multiple layers;
   means for delivering signals from each detection electrode of said second array of detection electrodes of said sensor means to a data acquisition system;
   means for analyzing signals received by said data acquisition system to determine the nature of the devices in said sensing space and to image a cross-section of the device; and
   a knowledge database associated with said means for analyzing signals received by said data acquisition system, said database being indexed such that data is used for back propagation for identifying concealed objects, said means for analyzing signals received by said data acquisition system to determine the nature of the devices in said sensing space and to image a cross-section of the device, comprising:
   architecture and means to implement image knowledge bases, which characterize objects, whose image attributes are acquired from multiple sensors.

9. A security scanning device for scanning, identifying and imaging the contents of devices in a sensing space, according to claim 8, said plurality of arrays of sensor means adjacent the sensing space being configured to enable implementation of data fusion to combine the complementary sensitivity of ECT and EMT to different material properties.

10. A security scanning device for scanning, identifying and imaging the contents of devices in a sensing space, according to claim 8, said means for delivering signals from each detection electrode of said second array of detection electrodes of said sensor means to a data acquisition system; being configured to enable determination of optimal techniques for noise filtering, feature extraction, construction of objects, generation of their attributes, and production of feedback signals to multiple image generation units, which utilize a variety of imaging technologies.

11. A security scanning device for scanning, identifying and imaging the contents of devices in a sensing space, according to claim 8, said database associated with said means for analyzing signals received by said data acquisition system, being configured to characterize objects, whose image attributes are acquired from multiple sensors, wherein image and knowledge data bases are built containing data regarding each of the known objects according to the process of:
   1) generating sets of primitives from the values of sensor signals that represent either (1) a discontinuity in intensity characteristic of segments of an edge of an object or (2) a range of values of adjacent sensor signals characteristic of one or more textures of the internal materials of an object;
   2) generating sets of higher-level primitives by association of several primitives to one another based on their spatial proximity and similarity of primitive values, so as to represent segments of edges and internal materials of said object by means of values of their attributes such as relative positions, sharpness, width, curvature and other characteristics derived from said sensor signals;

3) joining said higher-level primitives based on shared characteristics such as similarity of edges and internal materials to define the object;

4) generating a set of values of descriptors of said object such as object size, curvature and sharpness of its edges, metallic texture, unique chemical texture such as of nitrates, from said shared characteristics;

5) repeating Steps 1–4 with at least three other similar dangerous objects;

6) assigning weights to said descriptors, so that greater weight is given to descriptors with a similar and limited range of values and lesser or no weight is given to descriptors with dissimilar or widely varying ranges of values; and 7) reducing the sets of values of descriptors for each group of dangerous objects to a single set of descriptor values, ranges, and weights, each such set to be stored as a rule in a dangerous objects knowledge data base.

12. A security scanning device for scanning, identifying and imaging the contents of devices in a sensing space, according to claim 8, said plurality of arrays of sensor means adjacent the sensing space comprising:

capacitive and inductive sensors.

13. A security scanning device for scanning, identifying and imaging the contents of devices in a sensing space, according to claim 12, said database associated with said means for analyzing signals received by said data acquisition system being configured to characterize objects, whose image attributes are acquired from multiple sensors, wherein image and knowledge data bases are built containing data regarding each of the known objects according to a process comprising the steps of:

positioning known objects relative to capacitive and inductive sensors;

recording changes in capacitance and inductance in the vicinity of the capacitive and inductive sensors when each of a plurality of known objects is positioned in the vicinity;

building image and knowledge data bases containing data regarding each of the known objects;

moving luggage containing unknown objects relative to capacitive and inductive sensors;

comparing changes in capacitance and inductance in the vicinity of the unknown objects with data in the image and knowledge databases; and determining whether or not the object is a dangerous object.

14. A security scanning device for scanning, identifying and imaging the contents of devices in a sensing space, according to claim 11, said means to implement image knowledge bases, which characterize objects, whose image attributes are acquired from multiple sensors, comprising:

means to provide tomographic and non-tomographic images, in 2D or 3D, of dangerous objects and chemical substances, supported by knowledge-based image analysis and understanding for identifying dangerous objects and chemical substances.

15. A security scanning device for scanning, identifying and imaging the contents of devices in a sensing space, according to claim 8, said plurality of arrays of sensor means adjacent the sensing space comprising:

electrical capacitance sensors.

16. A security scanning device for scanning, identifying and imaging the contents of devices in a sensing space, according to claim 8, said means for developing a plurality of electric fields between at least one excitation electrode and each of a plurality of detection electrodes comprising:

means delivering high-frequency sine-wave excitation signals to said excitation electrode.

17. A security scanning device for scanning, identifying and imaging the contents of devices in a sensing space, according to claim 8, said means for analyzing signals received by said data acquisition system comprising:

phase sensitive demodulation for electrical tomography and knowledge-based imaging.

18. A security scanning device for scanning, identifying and imaging the contents of devices in a sensing space, according to claim 8, said plurality of arrays of sensor means adjacent the sensing space comprising:

a capacitive scanner with parallel sensor arrays.

19. A security scanning device for scanning, identifying and imaging the contents of devices in a sensing space, according to claim 8, said plurality of arrays of sensor means adjacent the sensing space comprising:

a plurality of electrodes, surrounding said sensing space.

20. A security device for scanning, identifying and imaging the contents of devices in a sensing space, according to claim 8, said plurality of arrays of sensor means adjacent the sensing space comprising:

a plurality of capacitance sensor arrays, wherein a plurality of excitation electrodes and a plurality of detection electrodes are mounted on a plate.

21. An electrical capacitance tomography (ECT) system for scanning, identifying and imaging the contents of devices in a sensing space comprising:

an array of excitation and detection electrodes adjacent the sensing space;

an excitation signal generator configured to apply a signal to at least one of said excitation electrodes to permit measurement of changes in capacitance between the excitation electrode and each of a plurality of detection electrodes;

means for deliver capacitance signals from each detection electrode to a data acquisition system; and means for analyzing capacitance signals received by said data acquisition system to determine the nature of the devices in said sensing space and to image a cross-section of the device, said capacitance signals received by said data acquisition system being positive when a device in said sensing space is dielectric material and negative when a device in said sensing space is metal, representing a negative change in capacitance, said means for analyzing signals received by said data acquisition system being configure to invert is the capacitance data during image reconstruction to permit imaging metallic devices using capacitance signals.

* * * * *